(12) United States Patent
Causey, III et al.

(10) Patent No.: US 8,579,813 B2
(45) Date of Patent: Nov. 12, 2013

(54) HANDHELD PERSONAL DATA ASSISTANT (PDA) WITH A MEDICAL DEVICE AND METHOD OF USING THE SAME

(75) Inventors: James D. Causey, III, Simi Valley, CA (US); Richard E. Purvis, Pasadena, CA (US); James L. Henke, Simi Valley, CA (US)

(73) Assignee: Medtronic Minimed, Inc., Northridge, CA (US)

( * ) Notice: Subject to any disclaimer, the term of this patent is extended or adjusted under 35 U.S.C. 154(b) by 889 days.

(21) Appl. No.: 10/429,385

(22) Filed: May 5, 2003

(65) Prior Publication Data

US 2004/0073095 A1 Apr. 15, 2004

Related U.S. Application Data

(63) Continuation of application No. 09/935,827, filed on Aug. 23, 2001, now Pat. No. 6,641,533, which is a continuation of application No. 09/487,423, filed on Jan. 20, 2000, now Pat. No. 6,558,320, which is a continuation of application No. 09/334,858, filed on Jun. 16, 1999, now Pat. No. 6,554,798, application No. 10/429,385, which is a continuation of application No. 09/377,472, filed on Aug. 19, 1999, now abandoned, and a continuation of application No. 09/334,996, filed on Jun. 17, 1999, now abandoned, and a continuation of application No. 09/246,661, filed on Feb. 5, 1999, now Pat. No. 6,248,067.

(60) Provisional application No. 60/096,994, filed on Aug. 18, 1998, provisional application No. 60/103,812, filed on Oct. 8, 1998.

(51) Int. Cl.
 *A61B 5/00* (2006.01)

(52) U.S. Cl.
 USPC ............ 600/301; 600/300; 600/316; 604/66; 128/897; 128/903

(58) Field of Classification Search
 USPC ................. 600/300–301; 128/903–905, 920; 604/65–68
 See application file for complete search history.

(56) References Cited

U.S. PATENT DOCUMENTS

| 4,270,532 A | 6/1981 | Franetzki et al. |
| 4,282,872 A | 8/1981 | Franetzki et al. |

(Continued)

FOREIGN PATENT DOCUMENTS

| EP | 0880936 A2 | 12/1998 |
| WO | 9728736 A1 | 8/1997 |

(Continued)

OTHER PUBLICATIONS

PCT International Search Report for PCT/US01/01670 dated May 9, 2001.

(Continued)

*Primary Examiner* — Bill Thomson
*Assistant Examiner* — Shirley Jian
(74) *Attorney, Agent, or Firm* — Medtronic MiniMed, Inc.

(57) ABSTRACT

A medical device module for use in a system with a remote programmer and/or a personal data assistant (PDA) with at least one medical device includes a housing, at least one medical device and a processor. The housing is adapted to couple with the PDA. The at least one medical device interface is coupled to the housing for interfacing with the at least one medical device. The processor is coupled to the at least one medical device interface to process data from the at least one medical device. The processor is also capable of interfacing with the PDA.

14 Claims, 17 Drawing Sheets

(56) References Cited

U.S. PATENT DOCUMENTS

| | | | |
|---|---|---|---|
| 4,373,527 A | 2/1983 | Fischell | |
| 4,494,950 A | 1/1985 | Fischell | |
| 4,731,726 A | 3/1988 | Allen, III | |
| 4,809,697 A | 3/1989 | Causey, III | |
| 4,871,351 A * | 10/1989 | Feingold | 604/66 |
| 5,050,612 A | 9/1991 | Matsumura | |
| 5,100,380 A | 3/1992 | Epstein et al. | |
| 5,307,263 A * | 4/1994 | Brown | 600/301 |
| 5,338,157 A | 8/1994 | Blomquist | |
| 5,390,671 A * | 2/1995 | Lord et al. | 600/347 |
| 5,417,222 A | 5/1995 | Dempsey et al. | |
| 5,507,288 A | 4/1996 | Bocker et al. | |
| 5,582,593 A | 12/1996 | Hultman | |
| 5,687,734 A | 11/1997 | Dempsey et al. | |
| 5,713,856 A * | 2/1998 | Eggers et al. | 604/65 |
| 5,772,586 A * | 6/1998 | Heinonen et al. | 600/300 |
| 5,871,465 A | 2/1999 | Vasko | |
| 5,876,351 A * | 3/1999 | Rohde | 600/523 |
| 5,885,245 A | 3/1999 | Lynch et al. | |
| 5,899,855 A | 5/1999 | Brown | |
| 5,913,310 A | 6/1999 | Brown | |
| 5,918,603 A | 7/1999 | Brown | |
| 5,925,021 A | 7/1999 | Castellano et al. | |
| 5,961,451 A | 10/1999 | Reber et al. | |
| 6,035,189 A * | 3/2000 | Ali-Vehmas et al. | 455/414.1 |
| 6,168,563 B1 * | 1/2001 | Brown | 600/301 |
| 6,175,752 B1 | 1/2001 | Say et al. | |
| 6,248,067 B1 | 6/2001 | Causey, III et al. | |
| 6,295,506 B1 | 9/2001 | Heinonen et al. | |
| 6,478,736 B1 * | 11/2002 | Mault | 600/300 |
| 6,540,672 B1 * | 4/2003 | Simonsen et al. | 600/300 |
| 6,694,191 B2 | 2/2004 | Starkweather et al. | |
| 7,156,808 B2 * | 1/2007 | Quy | 600/300 |
| 2001/0041920 A1 * | 11/2001 | Starkweather et al. | 607/60 |

FOREIGN PATENT DOCUMENTS

| | | | |
|---|---|---|---|
| WO | 0019887 | A1 | 4/2000 |
| WO | 0078210 | A1 | 12/2000 |
| WO | 0128416 | A1 | 4/2001 |
| WO | 0128495 | A2 | 4/2001 |
| WO | 0139089 | A1 | 5/2001 |
| WO | 0152718 | A2 | 7/2001 |
| WO | 0156454 | A2 | 8/2001 |

OTHER PUBLICATIONS

PCT Written Opinion for PCT/US01/01670 dated Nov. 16, 2001.
Response to PCT Written Opinion for PCT/US01/01670 dated Dec. 6, 2001.
PCT Written Opinion for PCT/US01/01670 dated Jan. 16, 2002.
Response to PCT Written Opinion for PCT/US01/01670 dated Feb. 19, 2002.
International Preliminary Examination Report for PCT/US01/01670 dated Mar. 1, 2002.

* cited by examiner

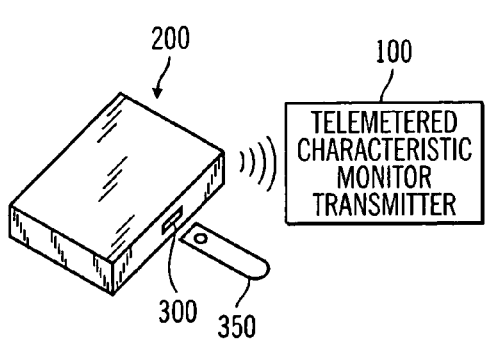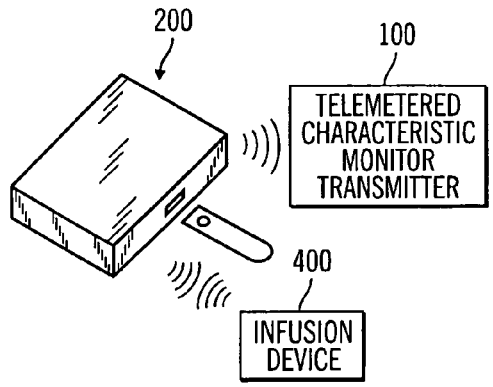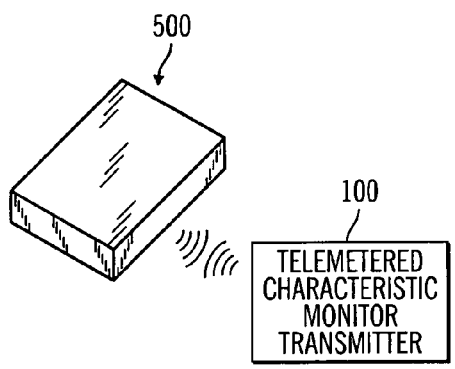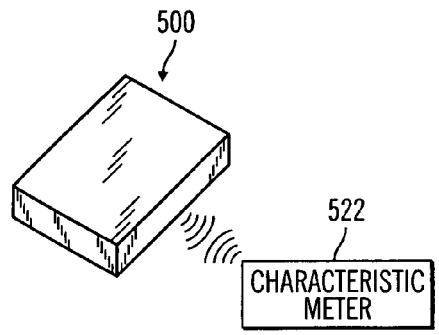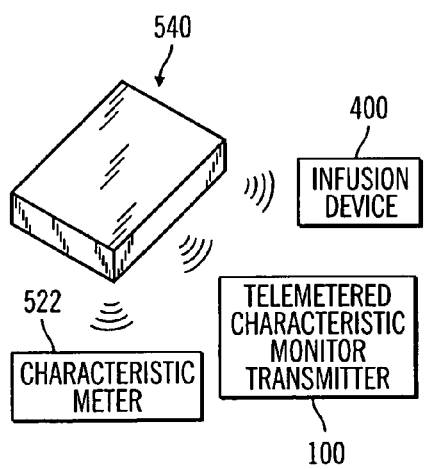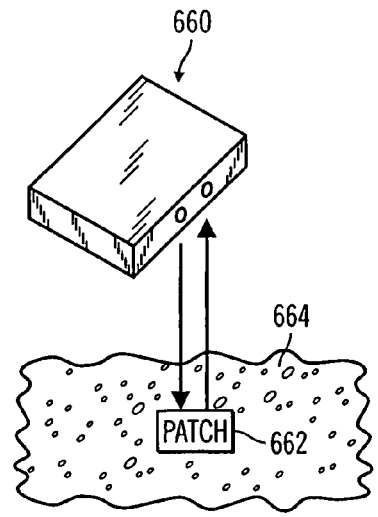

HANDHELD PERSONAL DATA ASSISTANT (PDA) WITH A MEDICAL DEVICE AND METHOD OF USING THE SAME

RELATED APPLICATIONS

This is a continuation of U.S. patent application Ser. No. 09/935,827 filed on Aug. 23, 2001 now U.S. Pat. No. 6,641,533, which is a continuation of U.S. patent application Ser. No. 09/487,423 filed Jan. 20, 2000 now U.S. Pat. No. 6,558,320, which is a continuation of U.S. patent application Ser. No. 09/334,858 filed Jun. 16, 1999 now U.S. Pat. No. 6,554,798 that claims priority on U.S. Provisional Application Ser. No. 60/096,994 filed Aug. 18, 1998, a continuation of U.S. application Ser. No. 09/377,472 filed Aug. 19, 1999 now abandoned that claims priority on U.S. Provisional Application Ser. No. 60/103,812 filed Oct. 8, 1998, a continuation of U.S. patent application Ser. No. 09/334,996 filed Jun. 17, 1999 now abandoned, and a continuation of U.S. patent application Ser. No. 09/246,661 filed Feb. 5, 1999—now U.S. Pat. No. 6,248,067, all of which are herein specifically incorporated by reference in their entirety.

FIELD OF THE INVENTION

This invention relates to remote programmers and/or handheld personal data assistants (PDA) for use with medical devices and, in particular embodiments, to a PDA that includes a medical device to facilitate testing and monitoring of a patient's condition with coordination of data management and programming through the PDA.

BACKGROUND OF THE INVENTION

Over the years, bodily characteristics have been determined by obtaining a sample of bodily fluid. For example, diabetics often test for blood glucose levels with a blood glucose meter. Traditional blood glucose determinations have utilized a painful finger stick using a lancet to withdraw a small blood sample that is used by the blood glucose meter. This results in discomfort from the lancet as it contacts nerves in the subcutaneous tissue. To obtain a measure of control or information on a diabetic's condition, several finger sticks and tests are required each day (8 or more such tests a day are not uncommon). The pain of lancing and the cumulative discomfort from multiple needle sticks is a strong reason why patients fail to comply with a medical testing regimen used to determine a change in characteristic over a period of time. In addition, these blood glucose meters are only designed to provide data at discrete points, and even with multiple tests a day, do not provide continuous data to show the variations in the characteristic between testing times.

A variety of implantable electrochemical sensors for use with monitors have been developed for detecting and/or quantifying specific agents or compositions in a patient's blood. For instance, glucose sensors have been developed for use in obtaining an indication of blood glucose levels in a diabetic patient. Such readings are useful in monitoring and/or adjusting a treatment regimen which typically includes the regular administration of insulin to the patient. Thus, blood glucose readings from the monitor improve medical therapies with semi-automated medication infusion pumps of the external type, as generally described in U.S. Pat. Nos. 4,562,751; 4,678,408; and 4,685,903; or automated implantable medication infusion pumps, as generally described in U.S. Pat. No. 4,573,994, which are herein incorporated by reference. Typical thin film sensors are described in commonly assigned U.S. Pat. Nos. 5,390,671; 5,391,250; 5,482,473; and 5,586,553 which are incorporated by reference herein. See also U.S. Pat. No. 5,299,571. However, the monitors and electrochemical sensors often require calibration using readings obtained from blood glucose meters to augment and adjust for drift over time. Thus, although the monitors and electrochemical sensors provide more accurate trend information, a separate blood glucose meter is still often required.

A user must often carry multiple devices to test different aspects of the same value or characteristic. For instance, the a user would need a blood glucose meter and blood glucose monitor. In addition, individuals are also carrying other electronic devices, such as an infusion device, cellular telephones, personal entertainment systems (such as radios, cassette players, CD players, or the like). They may also include small personal computers, personal data assistants (PDAs) or the like. Thus, users often carry a large number of separate electronic devices, which can be cumbersome and inconvenient to handle.

SUMMARY OF THE DISCLOSURE

It is an object of an embodiment of the present invention to provide an improved remote programmer and/or personal data assistant (PDA) that includes a characteristic monitor and/or a characteristic meter, which obviates for practical purposes, the above mentioned limitations.

According to an embodiment of the present invention a remote programmer for interfacing with at least one medical device includes at least one medical device module, at least one processor, a housing, at least one input/output port, at least one display, at least one button, at least one audio indication device and at least one portable power supply. The at least one medical device module is operatively coupled with the remote programmer and includes at least one medical device interface to interface with the at least one medical device. The at least one processor is to interface with the remote programmer and is coupled to the at least one medical device interface to process data from the at least one medical device. The housing is adapted to contain the medical device module and the at least one processor. The at least one input/output port is for communicating with the at least one medical device. The at least one display includes at least one touch screen element to interface with the at least one of the at least one processor and the at least one medical device. The at least one button is to interface with at least one of the at least one processor and the at least one medical device, and the at least one audio indication device is coupled to the at least one processor to provide an audio indication. The at least one portable power supply is contained within the housing of the remote programmer to provide power to at least one of the at least one processor and the at least one medical device. In still further embodiments, the at least one medical device is an infusion device, a characteristic monitor, a characteristic meter, an analyte sensor patch and/or more than one medical device. In other embodiments, the remote programmer is personal data assistant (PDA).

In particular embodiments, the at least one medical device module has a separate housing that is adapted to couple with the housing of the remote programmer. In other embodiments, the at least one medical device is a characteristic sensor that produces a signal indicative of a characteristic of a user, and further includes a second characteristic determining device. The second characteristic determining device is within the housing for receiving and testing an analyte to determine the quantity of the analyte independently of the at least one characteristic sensor. The at least one medical device interface is a sensor receiver to receive sensor data signals produced from the at least one characteristic sensor, and the at least one processor is coupled to the sensor receiver and the second characteristic determining device to process the determined quantity of the analyte from the second characteristic determining device and the sensor data signals from the at least one characteristic sensor. In further embodiments, the at least one characteristic sensor is remotely located from the at least one medical device module, and the sensor receiver receives the sensor data signals as wireless signals from the remotely located at least one characteristic sensor.

In other embodiments, the remote programmer further includes a transmitter coupled to the at least one processor and the input/output port for transmitting the processed sensor data signals to another data receiving device. In additional embodiments, the at least one medical device module uses the display of the remote programmer to show the determined quantity of the analyte from the second characteristic determining device and the processed sensor data signals from the at least one characteristic sensor. Also, the at least one processor monitors the sensor data signals from the sensor receiver to determine when the second characteristic determining device is to be used to perform calibration of the sensor data signals. In yet other embodiments, the remote programmer further includes at least one memory to store the determined quantity of the analyte from the second characteristic determining device and the processed sensor data signals from the at least one characteristic sensor. In particular embodiments, the sensor data signals are received by the sensor receiver continuously, near continuously or intermittently. In other embodiments, the second characteristic determining device is a second medical device module that utilizes a second characteristic sensor. In these embodiments, the determined quantity of the analyte from the second characteristic determining device is determined continuously, near continuously or intermittently.

In further embodiments of the present invention, the second medical device module and the second characteristic sensor use a different sensing technology from that used by the at least one medical device module and the characteristic sensor. In addition, the second characteristic determining device utilizes a discrete sample to determine the quantity of the analyte. Also, the second characteristic determining device may utilize a test strip to analyze the sample to determine the quantity of the analyte.

In yet further embodiments, the remote programmer further includes a transmitter coupled to the at least one processor and the input/output port. The at least one processor further includes the ability to program other medical devices, and the transmitter transmits a program to the other medical devices. In particular embodiments, the transmitter transmits through a relay device between the transmitter and a remotely located processing device. In some embodiments, the relay device increases a maximum distance by amplifying the processed sensor data signals from the transmitter to be received by the remotely located processing device. In other embodiments, the relay device enables the remotely located processing device to be located in a different room than the transmitter. While in other embodiments, the relay device includes a telecommunications device, and when the transmitter generates an alarm the telecommunications device transmits the alarm to a remotely located receiving station. Further embodiments of the remote programmer include a data receiver, and the data receiver receives program instructions from other processing devices.

In additional embodiments, a medical device module for use in a system with the at least one medical device and the remote programmer includes a module housing, the at least one medical device interface and at least one module processor. The module housing is adapted to couple with the housing of the remote programmer. The at least one medical device interface is coupled to the module housing for interfacing with the at least one medical device. The at least one module processor is coupled to the at least one medical device interface to process data from the at least one medical device, and wherein the at least one module processor is capable of interfacing with the at least one processor of the remote programmer.

In more embodiments, the at least one medical device is a characteristic sensor that produces a signal indicative of a characteristic of a user, and the medical device module further includes a second characteristic determining device. The second characteristic determining device is within the housing for receiving and testing an analyte to determine the quantity of the analyte independently of the at least one characteristic sensor. The at least one medical device interface is a sensor receiver to receive sensor data signals produced from the at least one characteristic sensor, and the at least one module processor is coupled to the sensor receiver and the second characteristic determining device to process the determined quantity of the analyte from the second characteristic determining device and the sensor data signals from the at least one characteristic sensor.

According to a further embodiment of the present invention, a medical device module for use in a system with a personal data assistant (PDA) with at least one medical device includes a housing, at least one medical device and a processor. The housing is adapted to couple with the PDA. The at least one medical device interface is coupled to the housing for interfacing with the at least one medical device. The processor is coupled to the at least one medical device interface to process data from the at least one medical device. The processor is also capable of interfacing with the PDA.

In preferred embodiments, the at least one medical device is a characteristic sensor that produces a signal indicative of a characteristic of a user, and the medical device module further includes a second characteristic determining device within the housing for receiving and testing an analyte to determine the quantity of the analyte independently of the at least one characteristic sensor. The at least one medical device interface is a sensor receiver to receive sensor data signals produced from the at least one characteristic sensor. The processor is coupled to the sensor receiver and the second characteristic determining device to process the determined quantity of the analyte from the second characteristic determining device and the sensor data signals from the at least one characteristic sensor.

In particular embodiments, the at least one characteristic sensor is remotely located from the medical device module, and the sensor receiver receives the sensor data signals as wireless signals from the remotely located at least one characteristic sensor. In other embodiments, the medical device module further includes a transmitter coupled to the processor for transmitting the processed sensor data signals to another data receiving device. In additional embodiments, the medical device module uses a display of the PDA to show the determined quantity of the analyte from the second characteristic determining device and the processed sensor data signals from the at least one characteristic sensor. In further embodiments, the processor monitors the sensor data signals from the sensor receiver to determine when the second characteristic determining device is to be used to perform calibration of the sensor data signals.

In other embodiments, the medical device module further includes a memory to store the determined quantity of the analyte from the second characteristic determining device and the processed sensor data signals from the at least one characteristic sensor. In still other embodiments, the sensor data signals are received by the sensor receiver continuously, near continuously or intermittently.

In yet another embodiments, the second characteristic determining device is a second medical device module that utilizes a second characteristic sensor. In these embodiments, the determined quantity of the analyte from the second characteristic determining device is determined continuously, near continuously or intermittently. In a further embodiment, the second medical device module and the second characteristic sensor use a different sensing technology from that used by the at least one medical device module and the characteristic sensor.

In still yet another embodiment of the present invention, the second characteristic determining device utilizes a discrete sample to determine the quantity of the analyte. In further embodiments, the second characteristic determining device utilizes a test strip to analyze the sample to determine the quantity of the analyte. In still further embodiments, the at least one medical device is an infusion device, an analyte sensor patch and/or more than one medical device.

Still other preferred embodiments of the present invention are directed to a personal data assistant (PDA) for interfacing with at least one medical devices described above. In these embodiments, the medical device module operatively couples with the PDA and the PDA includes a housing adapted to receive the medical device module.

Further preferred embodiments of the present invention are directed to a medical device module for use in a system with a personal data assistant (PDA) with at least one characteristic sensor that produces a signal indicative of a characteristic of a user. The medical device module includes a housing, a test strip receptacle, a sensor receiver and a processor. The housing is adapted to operatively couple with the PDA. The test strip receptacle for receiving and testing a test strip exposed to an analyte to determine the quantity of the analyte. The sensor receiver is for receiving sensor data signals produced from the at least one characteristic sensor. The processor is coupled to the sensor receiver and the test strip receptacle to process the determined quantity of the analyte from the test strip receptacle and the sensor data signals from the at least one characteristic sensor, and the processor is capable of interfacing with the PDA.

In particular embodiments, the at least one characteristic sensor is remotely located from the medical device module, and wherein the sensor receiver receives the sensor data signals as wireless signals from the remotely located at least one characteristic sensor. In other embodiments, the medical device module further includes a transmitter coupled to the processor for transmitting the processed sensor data signals to another data receiving device. Preferably, the transmitter transmits the processed sensor signals by radio frequencies. In additional embodiments, the transmitter transmits through a relay device between the transmitter and a remotely located processing device. Preferably, the relay device increases a maximum distance by amplifying the processed sensor data signals from the transmitter to be received by the remotely located processing device. Alternatively, the relay device enables the remotely located processing device to be located in a different room than the transmitter. In other alternative embodiments, the relay device includes a telecommunications device, and when the transmitter generates an alarm the telecommunications device transmits the alarm to a remotely located receiving station.

In further embodiments, the processor of the medical device module further includes the ability to program other medical devices, and wherein the transmitter transmits a program to the other medical devices. In still other embodiments, the medical device module further includes a data receiver, and the data receiver receives program instructions from other processing devices.

In yet another embodiment, the medical device module uses a display on the PDA to show the determined quantity of the analyte from the test strip receptacle and the processed sensor data signals from the at least one characteristic sensor. In still other embodiments, the processor of the medical device module the sensor data signals from the sensor receiver to determine when the test receptacle is to be used to perform calibration of the sensor data signals.

Additional embodiments of the medical device module further include a memory to store the determined quantity of the analyte from the test strip receptacle and the processed sensor data signals from the at least one characteristic sensor. In particular embodiments, the sensor data signals are received by the sensor receiver continuously, near continuously or intermittently.

Other features and advantages of the invention will become apparent from the following detailed description, taken in conjunction with the accompanying drawings which illustrate, by way of example, various features of embodiments of the invention.

BRIEF DESCRIPTION OF THE DRAWINGS

A detailed description of embodiments of the invention will be made with reference to the accompanying drawings, wherein like numerals designate corresponding parts in the several figures.

FIG. 6 is a perspective view of the medical device module that includes the characteristic meter and characteristic monitor that interfaces with a telemetered characteristic monitor transmitter in accordance with the embodiment of FIGS. 4 and 5.

FIG. 8 is a perspective view of the medical device module that includes the characteristic meter and characteristic monitor that interfaces with a telemetered characteristic monitor transmitter and interfaces with the infusion device in accordance with the embodiment of FIG. 7.

FIG. 11 is a perspective view of a medical device module that interfaces with a telemetered characteristic monitor transmitter in accordance with a fifth embodiment of the present invention.

FIG. 12 is a perspective view of a medical device module that interfaces with a characteristic meter in accordance with a sixth embodiment of the present invention.

FIG. 13 is a perspective view of a medical device module that interfaces with an infusion device, telemetered characteristic monitor transmitter and a characteristic meter in accordance with a seventh embodiment of the present invention.

FIG. 19 is a perspective view of a medical device module that interfaces with an implantable analyte sensing patch in accordance with a twelfth embodiment of the present invention.

DETAILED DESCRIPTION OF THE PREFERRED EMBODIMENTS

Figure 1:
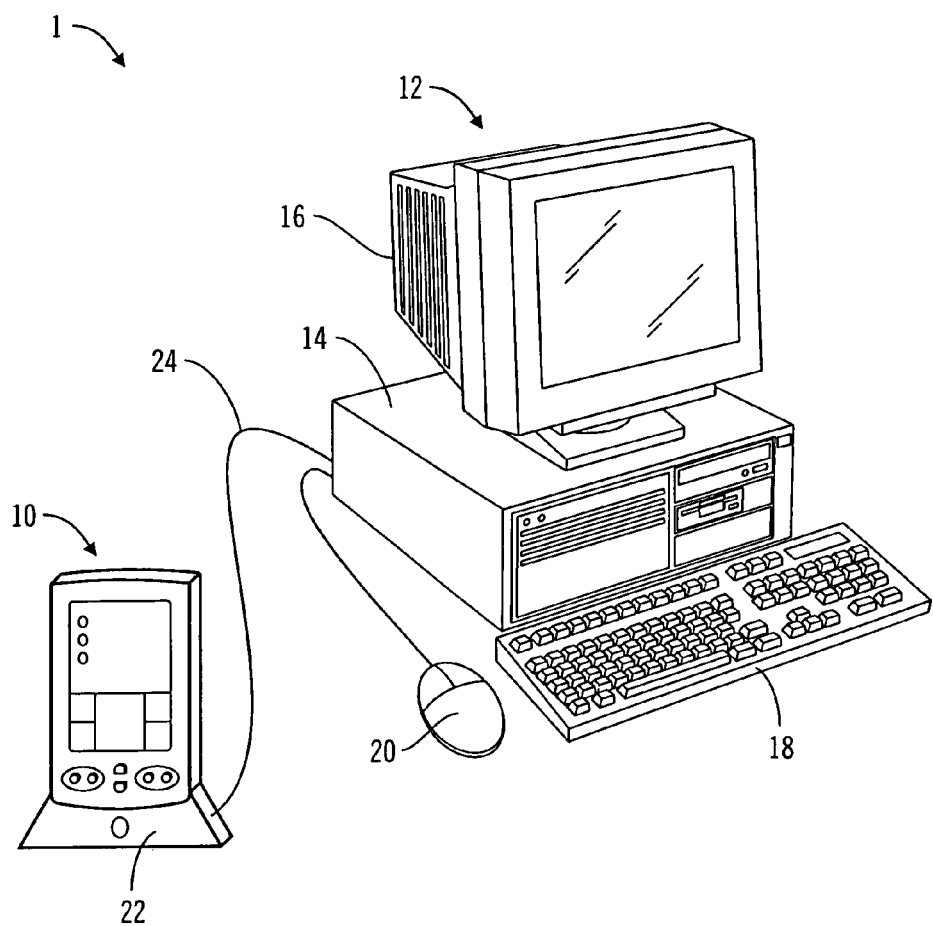
FIG. 1 is a perspective view of a system using a handheld data assistant (PDA) and computer in accordance with an embodiment of the present invention.

As shown in the drawings for purposes of illustration, the invention is embodied in a remote programmer and/or a handheld personal data assistant (PDA) that includes a medical device module for interfacing with a medical device. In preferred embodiments, medical device module interfaces with a characteristic monitor that obtains data from a telemetered characteristic monitor transmitter connected to a sensor set that determines body characteristics on a continuous, near continuous or intermittent basis. In further embodiments of the present invention, the medical device module interfaces with a characteristic meter for obtaining discrete measurements. In particular embodiments, the measurements received from the characteristic meter can be utilized by a characteristic monitor for calibration and/or data analysis and verification. In preferred embodiments, the characteristic monitor interfaces with a telemetered characteristic monitor transmitter that uses a sensor set and is for determining glucose levels in the blood and/or bodily fluids of the user. Preferably, the characteristic meter is primarily adapted for use with test strips that use a blood sample to determine glucose levels. However, other embodiments of the characteristic meter may use other testing structures, such as liquid samples placed in a receptacle, or the like, or test strips that use samples from other fluids, such as interstitial fluid, spinal fluid, saliva, urine, tears, sweat, or the like. However, it will be recognized that further embodiments of the invention may be used to interface with other telemetered characteristic monitors transmitters and/or meters to determine the levels of other agents, characteristics or compositions, such as hormones, cholesterol, medication concentrations, viral loads (e.g., HIV), or the like. In preferred embodiments, the characteristic monitor and sensor are primarily adapted for use with subcutaneous human tissue. However, still further embodiments may be placed in other types of tissue, such as muscle, lymph, organ tissue, veins, arteries or the like, and used in animal tissue. Other embodiments of the present invention may interface with other medical devices, such as pacemakers, implanted analyte sensor patches, infusion devices, telemetry devices, or the like.

Figure 21:
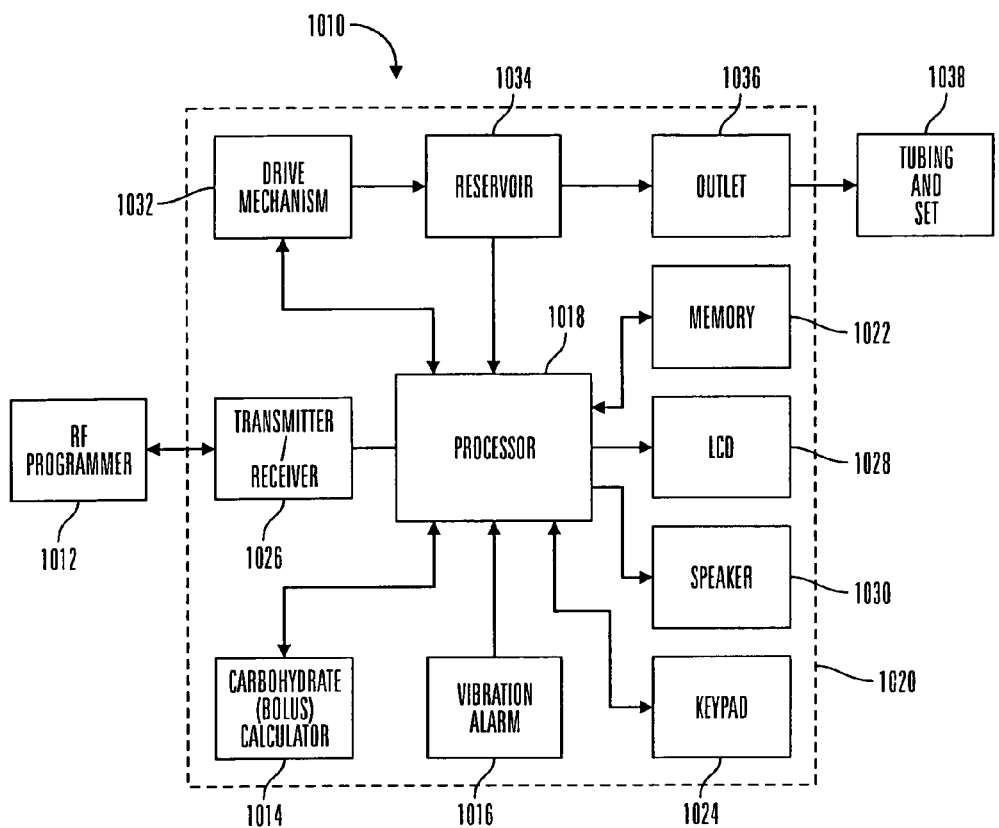
FIG. 21 is a simplified block diagram of an external infusion device and system in accordance with an embodiment of the present invention.

As illustrated in FIG. 21, preferred embodiments of the infusion device 1010 include a remote RF programmer 1012, a carbohydrate (or bolus) calculator 1014 and/or a vibration alarm 1016. The RF programmer 1012 and carbohydrate calculator 1014 communicate with a processor 1018 contained in a housing 1020 of the infusion device 1010. The processor 1018 is used to run programs and control the infusion device 1010, and is connected to an internal memory device 1022 that stores programs, history data, user defined information and parameters. In preferred embodiments, the memory device is a ROM and DRAM; however, in alternative embodiments, the memory device 1022 may include other memory storage devices such as RAM, EPROM, dynamic storage such as flash memory, energy efficient hard-drive, or the like. In preferred embodiments, the infusion device 1010 is an external infusion pump that is programmed through a keypad 1024 (including keys 1108, 1110, 1112 and 1114) on the housing 1020 or by commands received from the RF programmer 1012 through a transmitter/receiver 1026. Feedback to the infusion device 1010 on status or programming changes are displayed on an LCD 1028 and/or audibly through a speaker 1030. In alternative embodiments, the keypad 1024 may be omitted and the LCD 1028 may be used as a touch screen input device or the keypad 1024 may utilize more keys or different key arrangements then those illustrated in the figures. The processor 1018 is also coupled to a drive mechanism 1032 that is connected to a fluid reservoir containing fluid that is expelled through an outlet 1036 in the reservoir 1032 and housing 1020, and then into a body of a user through tubing and a set 1038. In further alternative embodiments, the keypad 1024, LCD 1020, speaker 1024 may be omitted and the infusion device is implanted in a body of the user, and all programming and data transfer is handled through the RF programmer 1012.

Figure 25:
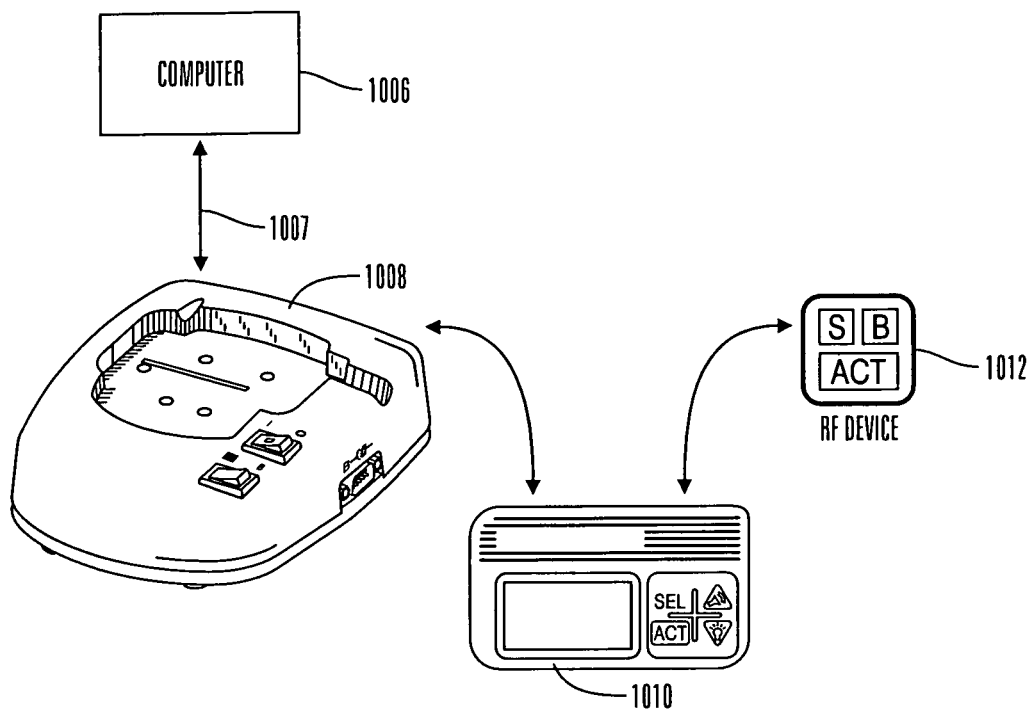
FIG. 25 is a simplified diagram of an external infusion device and system in accordance with another embodiment of the present invention.

Several programming options will be available in the infusion device 1010, and will include up to three customized basal profiles, a carbohydrate (or bolus) calculator and an alarm clock, as well as remote and on-device programming. Additionally, a physician/educator will be able to configure the infusion device 1010 through a Communications Station 1008 to provide or restrict access to certain programming options. Particular embodiments of the infusion device 1010 will also download stored information through the Communication-Station. Further description of a Communication Station of this general type is be found in U.S. Pat. No. 5,376,070 to Purvis et al., entitled DATA TRANSFER SYSTEM FOR AN INFUSION PUMP, which is herein incorporated by reference. This information can be used alone or combined with information from a Glucose Meter and/or a Glucose Sensor to assist the user and/or the health care professional in making intelligent therapy decisions. Moreover, the information, programs and data may be downloaded to a remote or local PC, laptop, station, or the like, for analysis and review by a MiniMed or a trained health care professional through the transmitter/receiver 1026. The data may also be downloaded through a Communication-Station 1008 to a remotely located computer 1006 such as a PC, lap top, or the like, over communication lines, by modem or wireless connection, as shown in FIG. 25.

The remote RF programmer 1012 (or remote commander) will enable the user to perform basic external infusion device 1010 programming steps without accessing the keyboard 1024 on the external infusion device 1010 or looking at the LCD (Liquid Crystal Display) 1028 screen. This will benefit visually impaired users of the external infusion device 1010, since the remote RF programmer 1012 will give them ready access to the most commonly used operations of the external infusion device 1010, and will obviate the need for visual feedback. Of particular importance to the sight impaired will be the auditory feedback (and/or vibration feedback as discussed below) that the external infusion device 1010 will provide. The instructions from the RF programmer 1012 will be confirmed by a series of audible beeps (or if requested by programming, vibration) from the external infusion device 1010. In alternative embodiments, the RF programmer 1012 may include a receiver and provide an audio (or vibration) indication that the commands have been received and acknowledged by the external infusion device 1010. In further embodiments, the keypad 1102 on the remote RF programmer 1012 will have the letters defining the capability of the key encoded in Braille, and the ridges that orient the user to the keypad 1102 will be quite pronounced to assist in guiding the user to the proper function key. Other embodiments may utilize keys that have different sizes or shapes to further enhance the ability for users to identify the correct buttons to activate the various features and functions.

A remote RF programmer 1012 will provide convenience and discretion for the user of the external infusion device 1010 by allowing concealment of the external infusion device 1010 under clothes, in pouches, or the like. Preferably, the RF programmer 1012 is an optional accessory item on the external infusion device 1010, and the external infusion device 1010 will be fully functional without the use of the RF programmer 1012. However, in alternative embodiments, the keypad 1024 in the external infusion device 1010 may be omitted and all programming would be handled by a local or remote PC, laptop, Communication-Station, RF programmer or the like. In preferred embodiments, the RF programmer 1012 will also provide the user with the ability to perform the following functions: deliver a bolus, suspend/restart the external infusion device, and set and cancel a temporary basal rate. However, in alternative embodiments, the RF programmer may include still additional capabilities such as data transfer (e.g., external infusion device history data or data from other medical devices), updates to software and programming, or the like. In preferred embodiments, the data transfer capabilities between the RF programmer 1012 and the transmitter/receiver 1026 of the external infusion device 1010 are two-way. In alternative embodiments, the data transfer from the RF programmer 1012 to the external infusion device 1010 is one-way, such that the RF programmer 1012 does not receive transmissions from the external infusion device 1010. In further embodiments, the RF programmer acts as a relay, or shuttle, for data transmission between the external infusion device 1010 and a PC, laptop, Communication-station, or the like.

Figure 26:
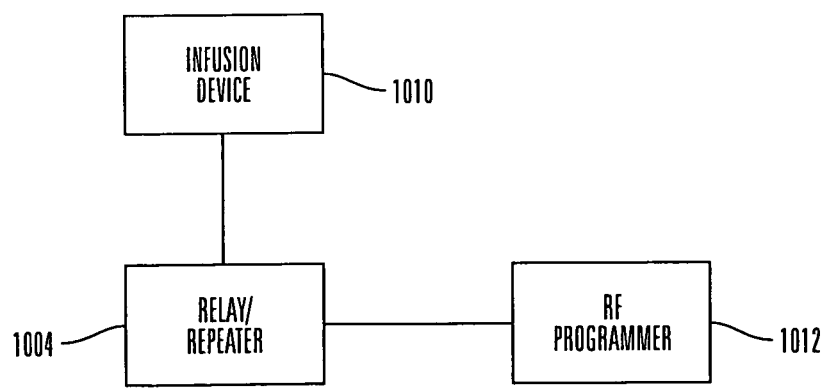
FIG. 26 is a simplified block diagram of an external infusion device and system in accordance with still another embodiment of the present invention.
Figure 27:
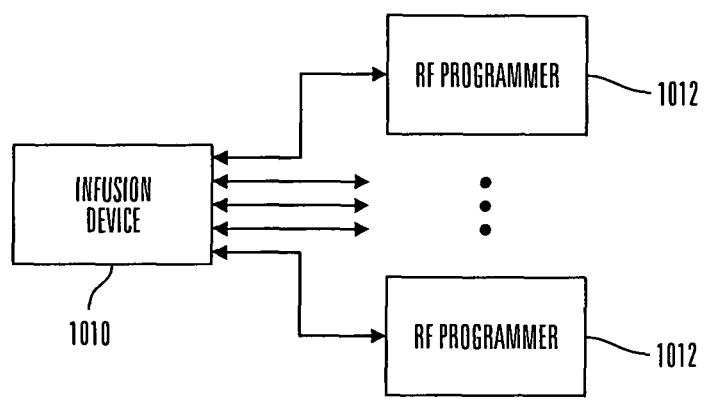
FIG. 27 is a simplified block diagram of an external infusion device and system in accordance with yet another embodiment of the present invention.

In addition, as shown in FIG. 26, a relay or repeater 1004 may be used with an external infusion device 1010 and an RF programmer 1012 to increase the distance from which the RF programmer 1012 can be used with the external infusion device 1010. For example, the relay could be used to provide information to parents of children using the external infusion device 1010 and allow them to program the external infusion device 1010 from a distance with the RF programmer 1012. The information could be used when children are in another room during sleep or doing activities in a location remote from the parents. In further embodiments, the relay 1004 can include the capability to sound an alarm. In addition, the relay 1004 may be capable of providing external infusion device 1010 information to a remotely located individual via a modem connected to the relay 1004 for display on a monitor, pager or the like. In a still further embodiment of the present invention, the external infusion device 1010 is capable of being programmed by multiple RF programmers 1012, as shown in FIG. 27. For instance, each RF programmer 1012 would learn (or be programmed with) the unique code (discussed below) of the external infusion device 1010. This would be useful for users that desired to have multiple RF programmers 1012, such as at home, office and/or school or needed a replacement for an RF programmer that was lost.

Figure 22:
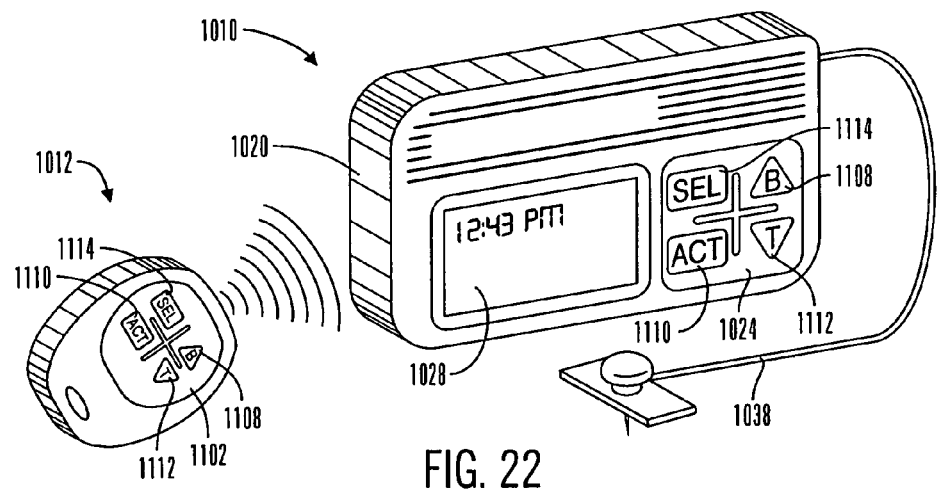
FIG. 22 is a perspective view of an external infusion device and system in accordance with an embodiment of the present invention.
Figure 23:
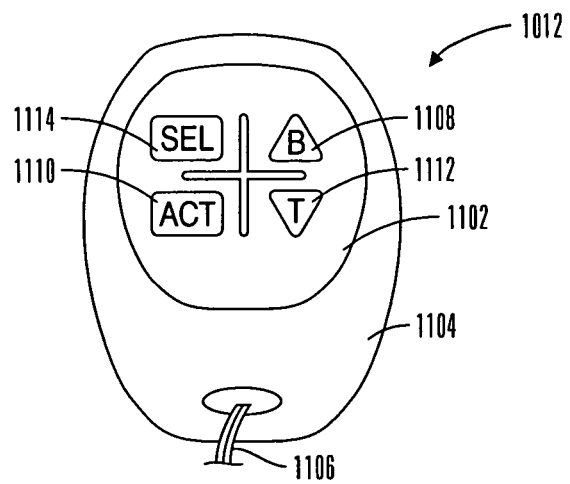
FIG. 23 is a top perspective view of an RF programmer in accordance with an embodiment of the present invention.

In preferred embodiments, the RF programmer 1012 is similar in appearance to the type of remote that is used to lock and unlock car doors. It will have four (4) keys on a keypad 1102 on a housing 1104, which will be laid out in a square grid pattern, similar in appearance and layout to the keypad 1024 on the infusion device 1010, as shown in FIGS. 22 and 23. In alternative embodiments, fewer keys may be used to simplify the RF programmer, reduce manufacturing costs and/or to reduce the number of program capabilities available. Preferably, the RF programmer 1012 should include a ring 1106 that fits on a key ring to lessen the likelihood that it is lost. It should also have a "quick release" feature to allow the user to disconnect it from the key ring.

Preferred embodiments utilize RF frequencies; however, alternative embodiments, may use optical, infrared (IR), ultrasonic frequencies, magnetic effects, or the like, to communicate with the external infusion device 1010.

Figure 24:
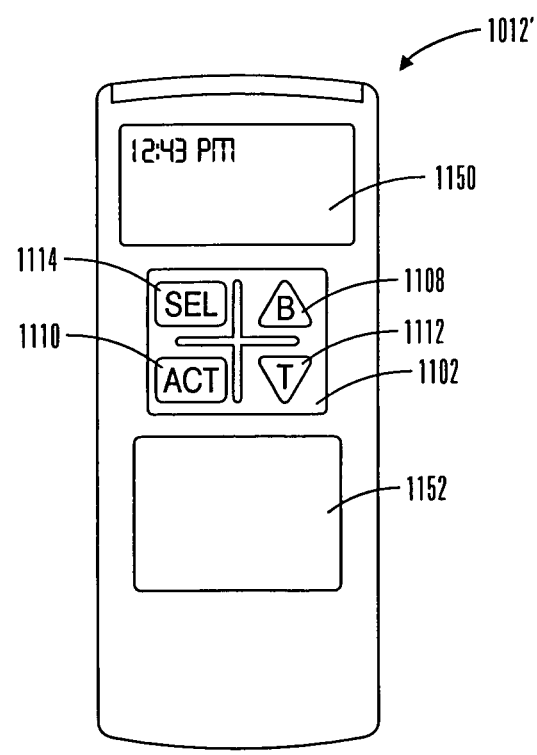
FIG. 24 is a top perspective view of a remote commander in accordance with another embodiment of the present invention.

Alternative embodiments of the RF programmer (controller or commander) 1012', as shown in FIG. 24, may have more complex keypad arrangements 1152, and may include a display device 1150, such as an LCD, LED, plasma screen, or the like, to assist in programming the external infusion device 1010. Further alternatives may include a microphone (not shown) and related circuitry to allow voice activated control of the external infusion device. In further alternative embodiments, the RF programmer 1012' may be formed in larger sizes, comparable to a TV controller or a pocket calculator, and may include a display to facilitate more complicated or easier programming. Still further embodiments, may include the ability to receive data and information from the external infusion device 1010 and/or a glucose monitoring device, and the ability to relay the information to another medical device, external infusion device 1010, glucose monitor device, PC, laptop, Communication-Station, or the like. Data transmission may be to other devices or include the capability to receive data or instructions. An RF activation capability may be included in addition to the programming capability.

In preferred embodiments, the external infusion device 1010 includes a receiver to receive the commands from the RF programmer 1012. Normally, the receiver is in a standby mode (e.g., not receiving) and becomes active for short periods every 2.5 seconds (approximately) to see if there is any RF activity from the RF programmer 1012. In alternative embodiments, the receiver of the external infusion device 1010 may be on continuously or may become active more often or less often, with the selection being dependent on power capacity, expected frequency of use of the RF programmer 1012, or the like. Generally, the receiver of the external infusion device 1010 requires that the RF programmer send an activating message for a period lasting about 5 seconds for the RF programmer to be recognized by the receiver. In alternative embodiments, longer or shorter periods of time for sending the activating message may be used.

Once the receiver recognizes that there is a valid RF programmer 1012 sending a message to the external infusion device 1010 (i.e., with this device 1010's unique code), the receiver will remain in an active mode until a complete sequence of commands has been received, or until the receiver times out due to a lack of RF communications from the RF programmer 1012. Preferably, upon recognition of a valid RF programmer 1012 trying to communicate with the receiver, the external infusion device 1010 will activate its audio beeper (or its vibrator or the like) to let the user know that the external infusion device 1010 has been activated by the RF programmer 1012. Typically, the receiver of the infusion device 1010 expects to receive a message with a valid preamble and message type, a recognized unique code, a valid function code (e.g., activate, bolus, suspend, or the like), an appropriate message count used by the receiver for reduction of RF interference problems, and a valid CRC on the transmitted message to ensure message integrity. Alternative embodiments, may include different message contents or components.

In operation, as discussed above, the RF programmer 1012 may be used to program several capabilities, such as an audio (or vibration) bolus, a suspension of external infusion device operation, a temporary basal rate, an extended bolus (such as square wave, ramp, triangular or the like) or dual wave bolus. In addition, the user may program a profiled bolus that uniquely matches the needs of the individual user (for instance it may contain square, ramp, pulse or curved portions that make up the profile to be delivered over a period of time). It should be noted that the capabilities may also be directly programmed on the external infusion device 1010 using the same sequence on the keypad of the external infusion device 1010.

The RF programmer 1012', since it includes a display 1150 may use the same programming protocol and key sequences as those used to program the external infusion device 1010 using the keypad 1024 and LCD 1028 on the external infusion device 1010. Alternatively, the RF programmer 1012' may use more sophisticated programming techniques, such as single key programming, if the display 1150 includes the capability to use touch screen techniques, or may use additional keys in the keypad 1152 that are specifically identified with particular programming features on the external infusion device 1010.

The Bolus estimator 1014 (or carbohydrate estimator that estimates a bolus based on carbohydrate consumption (CHO)) assists the user with carbohydrate counting and in determining precise dosing adjustments to account for meals. Carbohydrates are the primary, but not the only, factor affecting blood glucose levels. Generally, it is sufficient to account just for the carbohydrates. It also encourages the user to enter current blood glucose values before using this feature, which will also be viewed quite favorably by the health care professional, since it increases compliance with the medical regimen and improves control. In alternative embodiments, the bolus estimator 1014 in the external infusion device 1010 can be connected or coupled to a glucose monitor by way of the RF programmer 1012 (or other data transfer) to provide direct input to the bolus estimator 1014. In still further embodiments, the external infusion device 1010 may utilize a more complicated keypad and/or RF programmer 1012, and a code is assigned for each food. Then the code for each food to be consumed is entered into the external infusion device 1010. An example of Bolus Estimators can be found in U.S. Patent Application Ser. No. 60/096,994 filed Aug. 18, 1998 and is entitled "INFUSION DEVICE WITH REMOTE PROGRAMMING, CARBOHYDRATE CALCULATOR AND/ OR VIBRATION ALARM CAPABILITIES," or U.S. patent application Ser. No. 09/334,858 filed Jun. 17, 1999 and is entitled "EXTERNAL INFUSION DEVICE WITH REMOTE PROGRAMMING, BOLUS ESTIMATOR AND/ OR VIBRATION ALARM CAPABILITIES," both of which are herein incorporated by reference.

Further embodiments of the present invention include a vibration alarm 1016 that provides a noticeable vibration in addition to or in lieu of an audible alarm. The resulting tactile sensation of the vibration make the alarms more noticeable during sleep, when not thinking clearly due to various conditions, or the like, to improve the likelihood that the user will respond to an alarm. Thus, a vibration alarm 1016 can improve safety and control. In addition, the vibration alarm 1016 may be less publicly noticeable, and thus more useable in quiet settings, such as libraries, lectures, shows, or the like, or in loud settings where the alarm might go unnoticed, such as parties, concerts, or the like. In further embodiments, the RF programmer 1012 may include a vibration alarm (not shown) that can deliver a vibration alarm to the user in addition to, or instead of, the vibration alarm 1016 from the external infusion device 1010. Alternatively, the RF programmer 1012 may provide a vibration alarm and the external infusion device 1010 may provide an audible alarm or vice versa. In preferred embodiments, all alarms will gradually escalate in frequency or volume so that the user can terminate them as soon as they are noticed. In alternative embodiments, the alarms may change tones or intermittently stop to draw attention to the alarm condition. In further alternatives, the infusion device 1010 may use the transmitter/receiver 1026 to transmit the alarm to a remotely located device, such as a communication-station, modem or the like to summon help.

Figure 29:
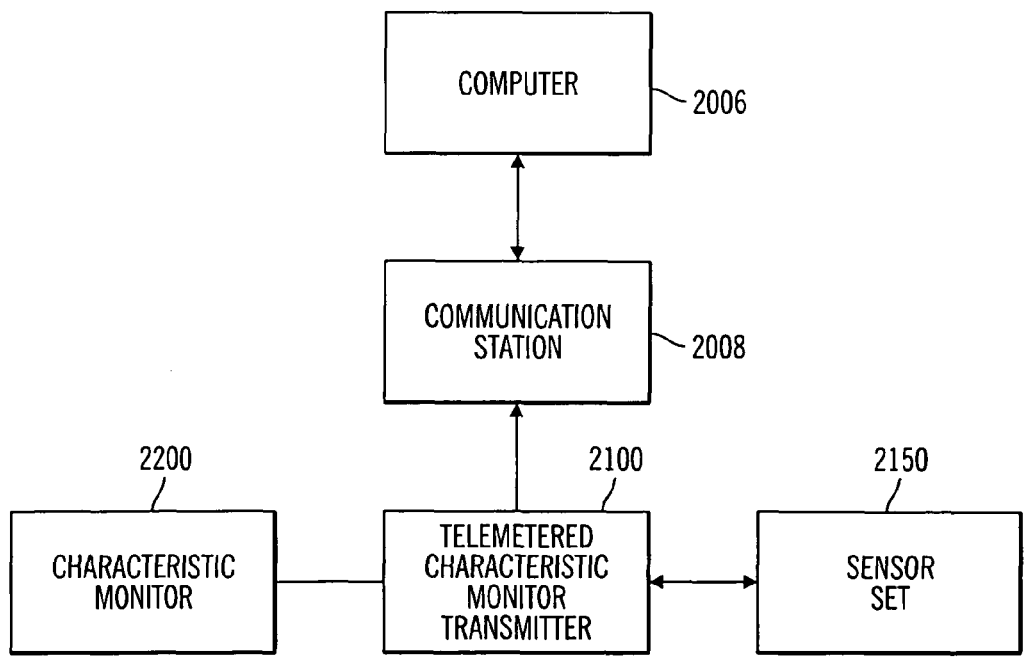
FIG. 29 is a simplified block diagram of a telemetered characteristic monitor transmitter and characteristic monitor system in accordance with still another embodiment of the present invention.
Figure 30:
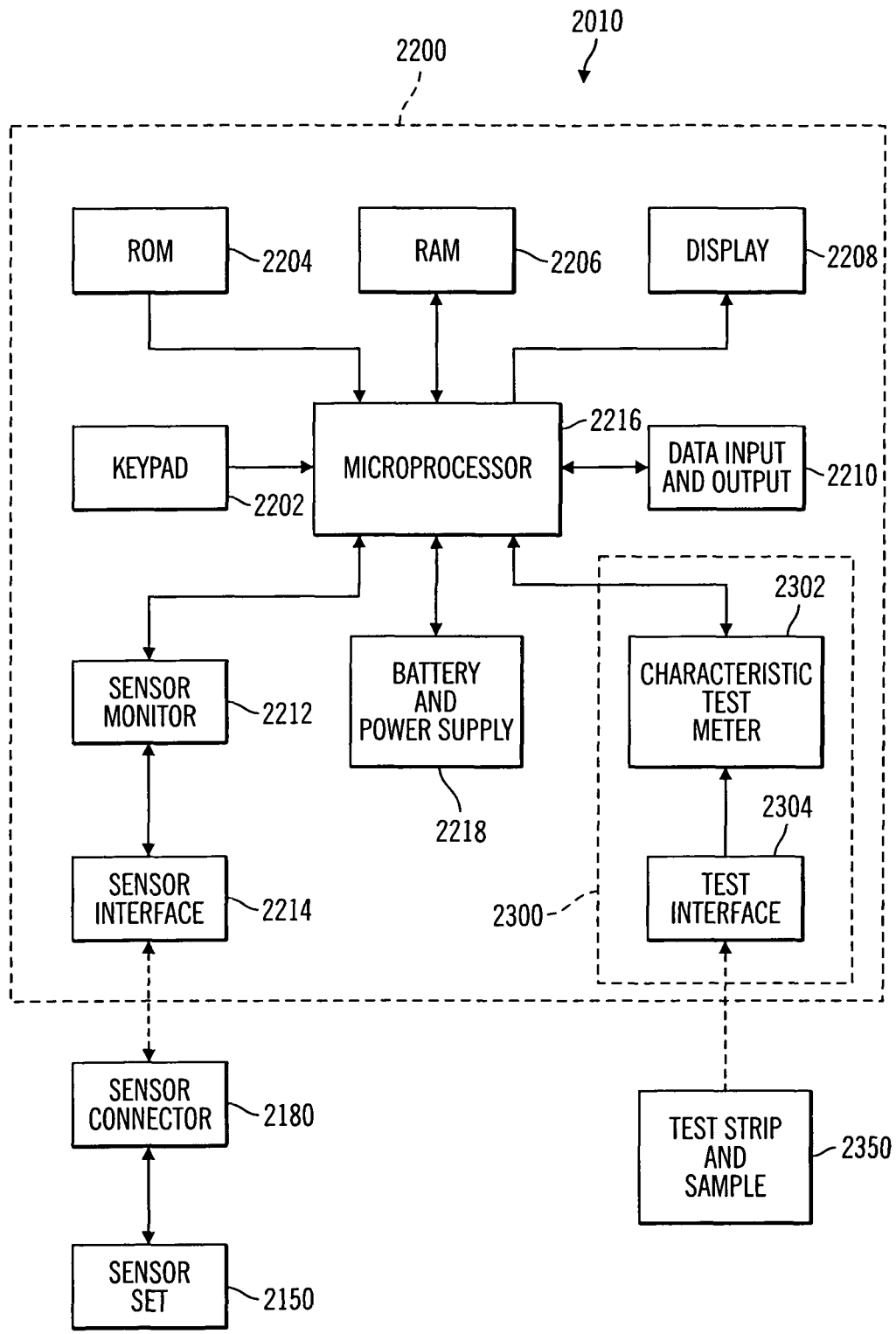
FIG. 30 is a simplified block diagram of a characteristic monitor with a characteristic meter in accordance with a first embodiment of the present invention.

In addition, as shown in FIG. 29, a relay 2004 may be capable of providing sensor set 2150 and telemetered characteristic monitor transmitter 2100 data to a remotely located individual via a modem connected to the relay 2004 for display on a monitor, pager or the like. The data may also be downloaded through a Communication-Station 2008 to a remotely located computer 2006 such as a PC, lap top, or the like, over communication lines, by modem or wireless connection, as shown in FIG. 29. Also, some embodiments may omit the Communication Station 2008 and uses a direct modem or wireless connection to the computer 2006. In further embodiments, the telemetered characteristic monitor transmitter 2100 transmits to an RF programmer, which acts as a relay, or shuttle, for data transmission between the sensor set 2150 and a PC, laptop, Communication-station, station, or the like. The telemetered characteristic monitor transmitter 2100 and characteristic monitor 2200 may also be combined with other medical devices to combine other patient data through a common data network and telemetry system.

As shown in FIGS. 30-33, a characteristic monitor 2200 may include a display 2208 that is used to display the results of the measurement received from the sensor in the sensor set 2150 via the telemetered characteristic monitor transmitter 2100. The results and information displayed includes, but is not limited to, trending information of the characteristic (e.g., rate of change of glucose), graphs of historical data, average characteristic levels (e.g., glucose), or the like. Alternative embodiments include the ability to scroll through the data. The display 2208 may also be used with a keypad 2202 on the characteristic monitor to program or update data in the characteristic monitor 2200. It is noted that the typical user can be expected to have somewhat diminished visual and tactile abilities due to complications from diabetes or other conditions. Thus, the display 2208 and keypad 2202 should be configured and adapted to the needs of a user with diminished visual and tactile abilities. In alternative embodiments, the value can be conveyed to the user by audio signals, such as beeps, speech or the like. Still further embodiments may use a touch screen instead of (or in some cases addition to) keypad 2202 to facilitate water proofing and to ease changes in the characteristic monitor 2200 hardware to accommodate improvements or upgrades.

In further embodiments of the present invention, the characteristic monitor 2200 may be replaced by a different device. For example, in one embodiment, the telemetered characteristic monitor transmitter 2100 communicates with an RF programmer (see FIGS. 1-29) that is also used to program and obtain data from an infusion pump 1010 or the like. The RF programmer may also be used to update and program the transmitter 2100, if the transmitter 2100 includes a receiver for remote programming, calibration or data receipt. The RF programmer can be used to store data obtained from the sensor set 2150 and then provide it to either an infusion pump 1010, characteristic monitor, computer or the like for analysis. In further embodiments, the transmitter 2100 may transmit the data to a medication delivery device, such as an infusion pump or the like, as part of a closed loop system. This would allow the medication delivery device to compare sensor results with medication delivery data and either sound alarms when appropriate or suggest corrections to the medication delivery regimen. In preferred embodiments, the transmitter 2100 would include a transmitter to receive updates or requests for additional sensor data. An example of one type of RF programmer can be found in U.S. Patent Application Ser. No. 60/096,994 filed Aug. 18, 1998 and is entitled "INFUSION DEVICE WITH REMOTE PROGRAMMING, CARBOHYDRATE CALCULATOR AND/OR VIBRATION ALARM CAPABILITIES," or U.S. patent application Ser. No. 09/334,858 filed Jun. 17, 1999 and is entitled "EXTERNAL INFUSION DEVICE WITH REMOTE PROGRAMMING, BOLUS ESTIMATOR AND/OR VIBRATION ALARM CAPABILITIES," both of which are herein incorporated by reference.

In further embodiments, the telemetered characteristic monitor transmitter 2100 can include a modem, or the like, to transfer data to and from a healthcare professional. Further embodiments, can receive updated programming or instructions via a modem connection.

As shown in FIGS. 30-33, in preferred embodiments, the microprocessor 2216 is coupled to a data input and output (I/O) port 2210, and the user can download the stored information to an external computer (see FIGS. 1, 10 and 29), or the like, through the data I/O port 2210 for evaluation, analysis, calibration, or the like. Preferably, the data I/O port 2210 is capable of transferring data in both directions so that updated program instructions or reminder alarms can be set by the user or doctor. In preferred embodiments, the I/O port 2210 uses infrared (IR) technology, such as that shown and described in U.S. Pat. No. 5,376,070 entitled "Data Transfer System for an Infusion Pump", or the like, which is herein incorporated by reference. However, in alternative embodiments, the I/O port 2210 may use other data transfer technologies such as cables, fiber optics, RF, or the like. In still other embodiments, the data I/O port 2210 may include multiple ports to support multiple communication protocols or methods, or may include a universal port capable of transmitting data in several different modes. In preferred embodiments, the stored data may be downloaded to (or new program instructions and data uploaded from) a computer, communication station, or the like. In alternative embodiments, the stored data may be downloaded to (or new program instructions and data uploaded from) an infusion pump, or the like. In preferred embodiments, the characteristic monitor 2200 is the approximate size of a conventional glucose meter or smaller. However, in alternative embodiments, the characteristic monitor 2200 may be formed in larger sizes, comparable to a TV controller or a pocket calculator, and may include a larger display 2208 to facilitate more complicated or easier programming.

The keypad 2202 provides the user with the capability to store additional information, set the date and the time, or set alarms to indicate when to take the next test with the characteristic meter 2300. The keypad 2202 is used in conjunction with the display 2208 to access the various modes, alarms, features, or the like, by utilizing methods typically employed to set the parameters on a conventional glucose meter, an infusion pump, or the like. The keypad 2202 may also be used to manipulate the stored data in the characteristic monitor 2200 and display the data on the on-board display 2208.

The programs for controlling the sensor monitor 2212 of the characteristic monitor 2200 are also stored in the ROM 2204, and sensor data signal values received by the sensor interface 2214 from the sensor set 2150 are processed by the sensor monitor 2212 and the microprocessor 2216, and then the results are stored in the RAM 2206. The sensor monitor 2212 and the sensor interface 2214 can be activated by a wired connection to a sensor set 2150 that draws power from the characteristic monitor, by receipt of a signal from the telemetered characteristic monitor transmitter 2100, or by the keypad 2202. Preferred embodiments use a characteristic monitor 2200 (in which the system includes a Potentiostat such as sensor monitor 2212) to receive the sensor signals from a telemetered characteristic monitor transmitter 2100, as shown in U.S. Patent Application Ser. No. 60/103,812 entitled "Telemetered Characteristic Monitor System and Method of Using the Same", which is herein incorporated by reference. In alternative embodiments, the sensor signals may be received on a more infrequent (or periodic) basis from a Holter-type monitor system, as shown in U.S. patent application Ser. No. 09/246,661 entitled "An Analyte Sensor and Holter-type Monitor System and Method of Using the Same", which is herein incorporated by reference.

As shown in FIGS. 30-33, the characteristic monitor 2200 includes a display 2208 that is used to display the results of the measurement received from the sensor in the sensor set 2150 via a cable and connector 2180 attached to the telemetered characteristic monitor transmitter 2100, or the like. In preferred embodiments, the display device 2208 is an active matrix LCD. However, alternative embodiments may use other display devices, such as simplified LCD, LED, fluorescent element, plasma screen, or the like. The results and information displayed includes, but is not limited to, trending information of the characteristic (e.g., rate of change of glucose), graphs of historical data, average characteristic levels (e.g., glucose), or the like. Alternative embodiments include the ability to scroll through the data. The display 2208 may also be used with the keypad 2202 on the characteristic monitor 2200 to program or update data in the characteristic monitor 2200. In addition, the calibrated data using results from the characteristic meter 2300 can be displayed to provide a user with updated trend and glucose level data. This may also be used to update and show differences between the newly calibrated (or additional calibration) data and the data as it was prior to the new calibration (or additional calibration).

In other embodiments, if multiple characteristic sensors are used, the individual data for each characteristic sensor may be stored and displayed to show a comparison and an average between the two characteristic sensors.

It is noted that a typical user can have somewhat diminished visual and tactile abilities due to complications from diabetes or other conditions. Thus, the display 2208 and keypad 2202 are preferably configured and adapted to the needs of a user with diminished visual and tactile abilities. In alternative embodiments, the data, analyte level value, confirmation of information, or the like can be conveyed to the user by audio signals, such as beeps, speech or the like, or vibrations. Still further embodiments may use a touch screen instead of (or in some cases addition to) the keypad 2202 to facilitate water proofing and to minimize changes in the characteristic monitor 2200 hardware to accommodate improvements or upgrades. Additional embodiments of the present invention may include a vibrator alarm (or optional indicator such as an L.E.D.) in either, or both, the telemetered characteristic monitor transmitter 2100 and the characteristic monitor 2200 to provide a tactile (vibration) alarm to the user, such as sensor set 2150 malfunction, improper connection, low battery, missed message, bad data, transmitter interference, or the like. The use of a vibration alarm provides additional reminders to an audio alarm, which could be important to someone suffering an acute reaction, or where it is desirable to have non-audio alarms to preserve and conceal the presence of the characteristic monitor system 2010.

Figure 33:
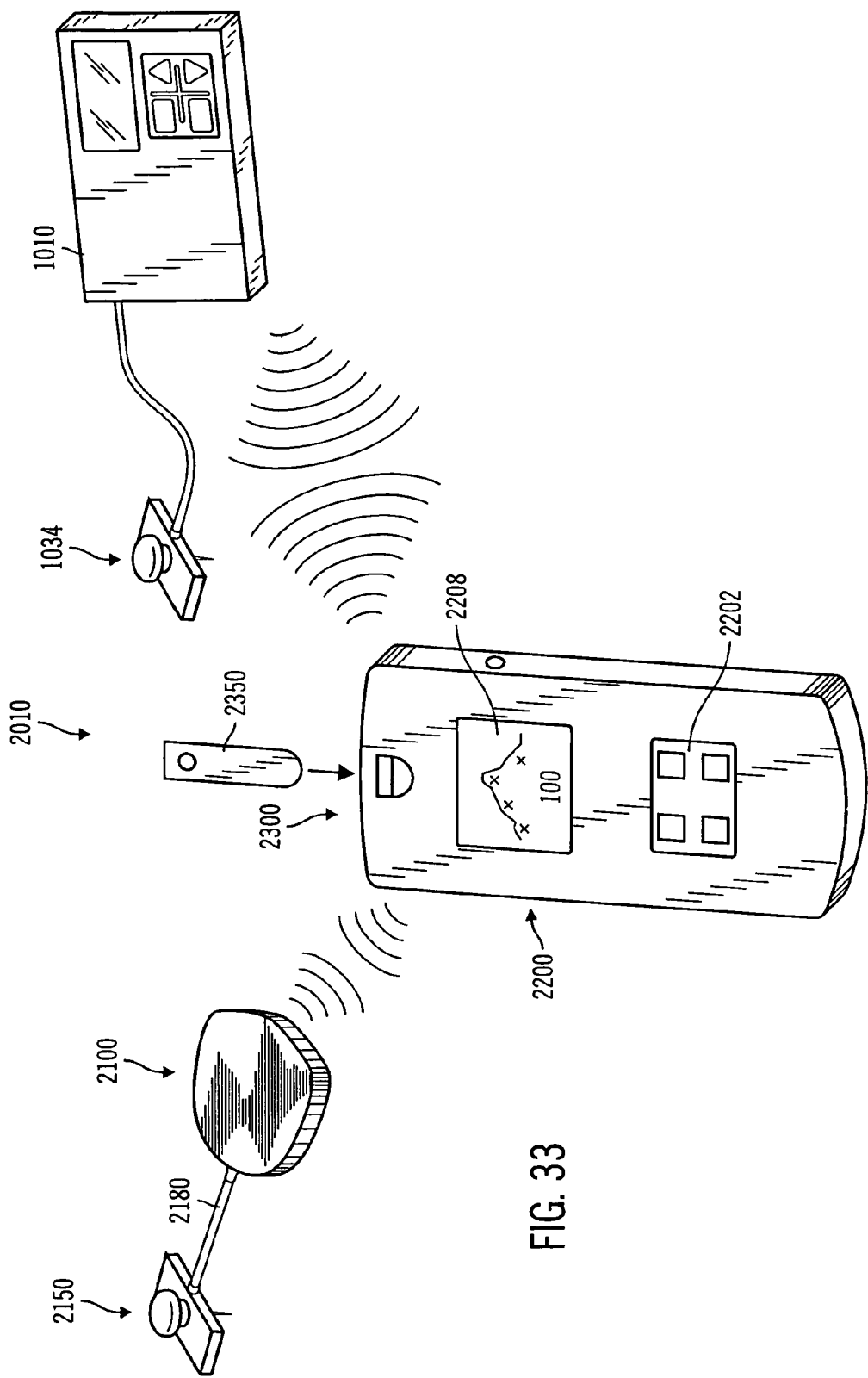
FIG. 33 is a perspective view of a characteristic monitor with a characteristic meter for use with a telemetered glucose sensor and an infusion pump in accordance with a third embodiment of the present invention.

As shown in FIG. 33, further embodiments of the characteristic monitor 2200 may be used with a telemetered characteristic monitor transmitter 2100 coupled to a sensor set 2150 and an infusion pump 1010 connected to an infusion set 1038. In this embodiment, the characteristic monitor 2200 is also used to program and obtain data from the infusion pump 1010, or the like. This further reduces the amount of equipment, the user must have, since the characteristic monitor 2200 already includes a characteristic meter 2300 that will be required for calibration of the data from the telemetered characteristic monitor transmitter 2100. Thus, the characteristic monitor 2200 can coordinate the sensor data and meter data with the data from the infusion pump 1010, or update the delivery parameters of the infusion pump 1010. The characteristic monitor 2200 may also be used to update and program the telemetered characteristic monitor transmitter 2100, if the transmitter 2100 includes a receiver for remote programming, calibration or data receipt. Thus, the user may need only a single device—the characteristic monitor 2200 that will receive data from a sensor set 2150, perform discrete tests of an analyte with the characteristic meter 2300, program and control an infusion pump 1010, and operate to download data or upload programming instructions to a computer, communication station, or the like.

Figure 28:
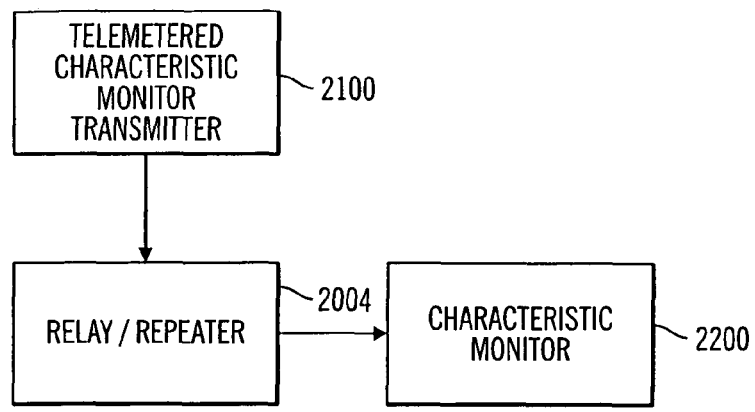
FIG. 28 is a simplified block diagram of a telemetered characteristic monitor transmitter and characteristic monitor in accordance with another embodiment of the present invention.
Figure 31:
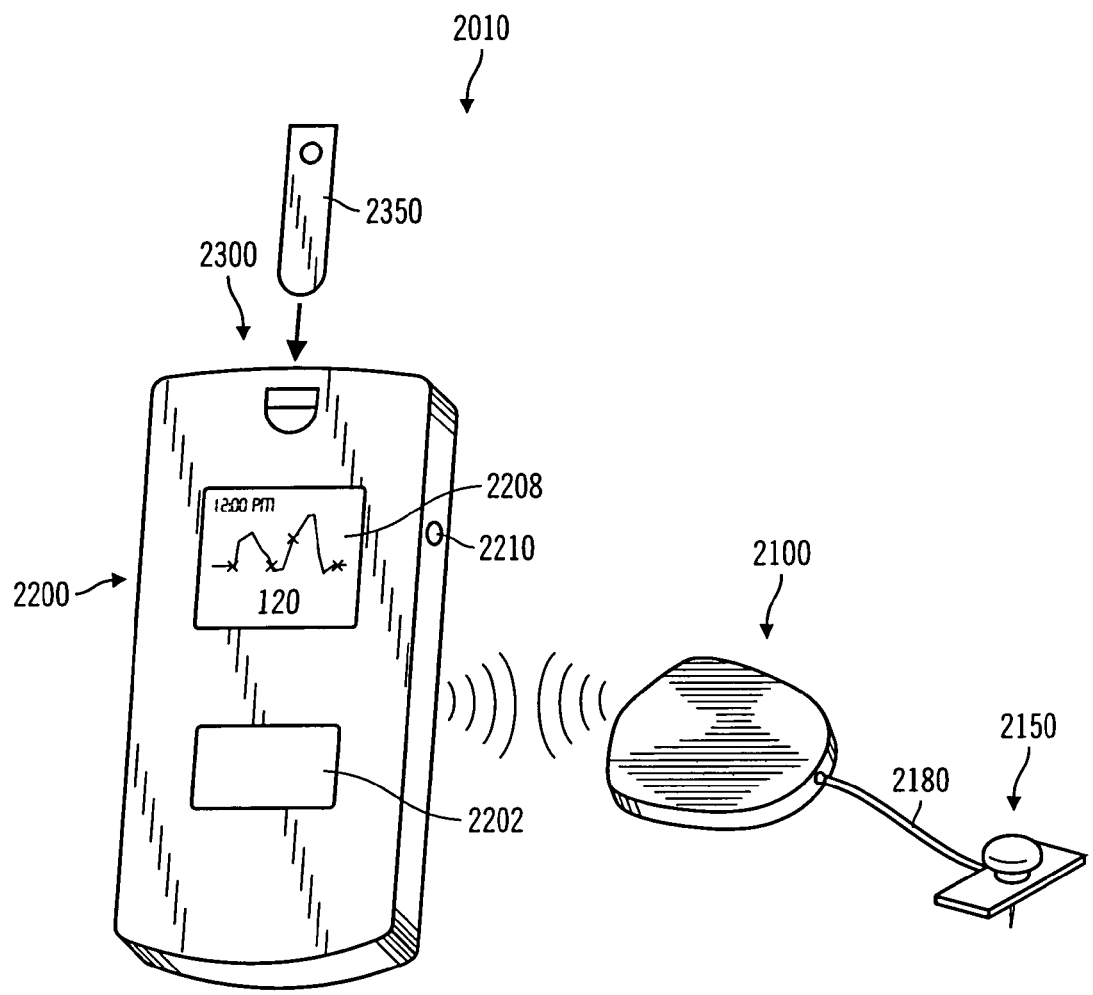
FIG. 31 is a perspective view of a characteristic monitor with a characteristic meter in accordance with a first embodiment of the present invention.
Figure 32:
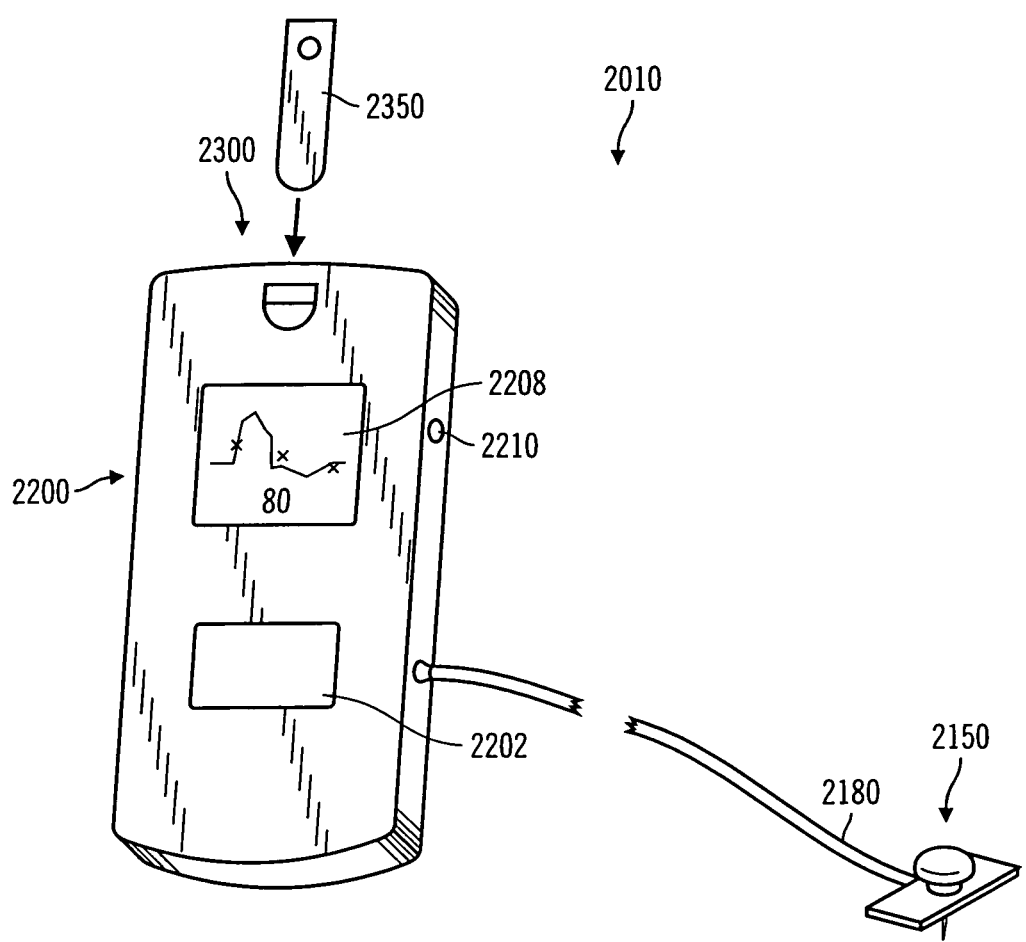
FIG. 32 is a perspective view of a characteristic monitor with a characteristic meter in accordance with a second embodiment of the present invention.

As discussed, the characteristic monitor 2200 can also be used to store data obtained from the sensor set 2150 and then provide it to either an infusion pump 1010, computer or the like for analysis. In further embodiments, the characteristic monitor 2200 can include a modem, or the like, to transfer data to and from a healthcare professional. Further embodiments, can receive updated programming or instructions via a modem connection. In addition, a relay or repeater 2004 may be used with a telemetered characteristic monitor transmitter 2100 and a characteristic monitor 2200 to increase the distance that the telemetered characteristic monitor transmitter 2100 can be used with the characteristic monitor 2200, as shown in FIG. 28. For example, the relay 2004 could be used to provide information to parents of children using the telemetered characteristic monitor transmitter 2100 and the sensor set 2150 from a distance. The information could be used when children are in another room during sleep or doing activities in a location remote from the parents. In further embodiments, the relay 2004 can include the capability to sound an alarm. In addition, the relay 2004 may be capable of providing data from sensor set 2150 and telemetered characteristic monitor transmitter 2100 to a remotely located individual via a modem connected to the relay 2004 for display on a monitor, pager or the like. In alternative embodiments, the data from the characteristic monitor 2200 and sensor set 2150 may also be downloaded through a communication station 2008 (or alternatively, through a characteristic monitor 2200, other data transfer device, or the like) to a remotely located computer 2006 such as a PC, lap top, or the like, over communication lines, by modem or wireless connection, as shown in FIG. 29. Also, some embodiments may omit the communication station 2008 and use a direct modem or wireless connection to the computer 2006. In further alternatives, either the characteristic monitor 2200 or the telemetered characteristic monitor transmitter 2100 may transmit an alarm to a remotely located device, such as a communication-station, modem or the like to summon help. In addition, further embodiments of the characteristic monitor 2200 may include the capability for simultaneous monitoring of multiple sensors. Data transmission may be to other devices or include the capability to receive data or instructions from other medical devices. Preferred embodiments, as shown in FIGS. 31 and 33, use wireless RF frequencies; however, alternative embodiments may utilize IR, optical, ultrasonic, audible frequencies or the like. Further embodiments may also use a wired connection, as shown in FIG. 32.

Preferably, the characteristic monitor system 2010 combines the characteristic monitor 2200 and character meter 2300 into a single device, but avoids an actual wired connection to the sensor set 2150 by using a telemetered characteristic monitor transmitter 2100. By separating the characteristic monitor system 2010 electronics into two separate devices; a telemetered characteristic monitor transmitter 2100 (which attaches to the sensor set 2150) and a characteristic monitor 2200, several advantages are realized. For instance, the user can more easily conceal the presence of the characteristic monitor system 2010, since a wire will not be visible (or cumbersome), with clothing. In also makes it is easier to protect the characteristic monitor 2200, which can be removed from the user's body during showers, exercise, sleep or the like. In addition, the use of multiple components (e.g., transmitter 2100 and characteristic monitor 2200 with a characteristic meter) facilitates upgrades or replacements, since one module or the other can be modified or replaced without requiring complete replacement of the characteristic monitor system 2010. Further, the use of multiple components can improve the economics of manufacturing, since some components may require replacement on a more frequent basis, sizing requirements may be different for each module, there may be different assembly environment requirements, and modifications can be made without affecting the other components.

FIG. 1 is a perspective view of a system 1 using a handheld data assistant (PDA) 10 and computer 12 in accordance with an embodiment of the present invention. Preferred embodiments, use a PDA 10 such as the Visor 1003E by Handspring. However, alternative embodiments, may use standard or customized personal data assistants such as, but not limited to, the Palm Pilot, Palm III, Palm V and/or Palm VII by Palm Computing a division of 3 COM, the PCS NP 1000 by Sprint, the pdQ 1900 by Qualcomm, the AutoPC by Clarion, Newton by Apple, the Cassiopeia by Casio, Blackberry by Research In Motion Limited, or the like. In preferred embodiments, the computer 12 includes a computer processing unit 14, a monitor 16, a key board 18 and a mouse 20. The computer 12 also includes a PDA cradle 22 connected to the computer 12 by a cable 24 to provide two-way data communication between the PDA 10 and the computer 12. In alternative embodiments, the PDA cradle 22 may connect to the computer using a wireless connection. In further alternative embodiments, the PDA cradle 22 may be omitted and the PDA 10 includes a receiver and transmitter and/or a jack to provide the two-way communication between the PDA 10 and the computer 12. In further alternative embodiments, the computer 12 may be replaced with a different processing device, such as a data processor, a laptop computer, a modem or other connection to a network computer server, an internet connection, or the like.

Figure 2:
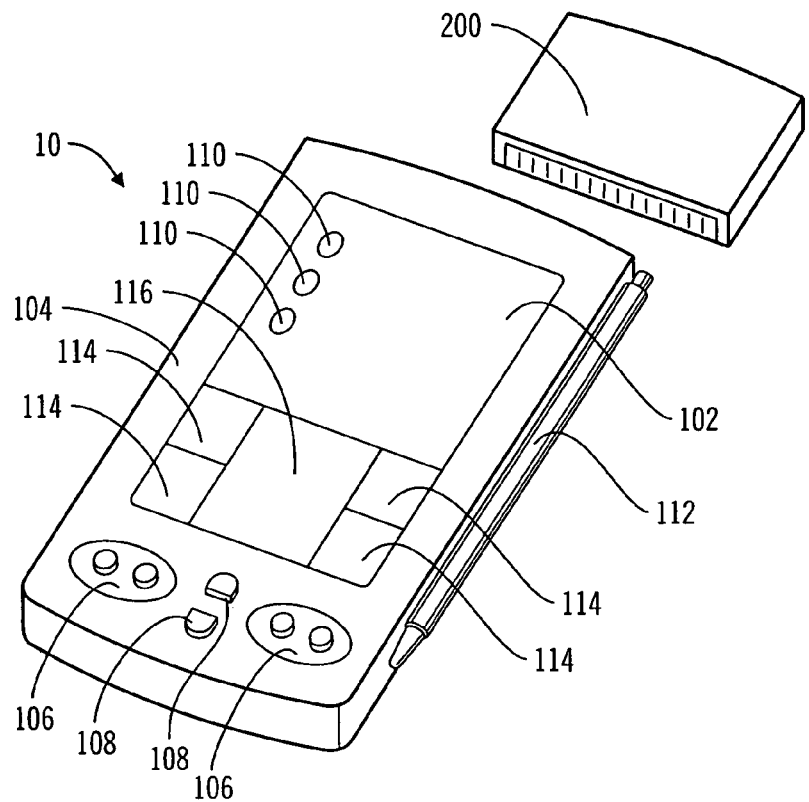
FIG. 2 is a perspective view of a PDA with a medical device module in accordance with an embodiment of the present invention.
Figure 3:
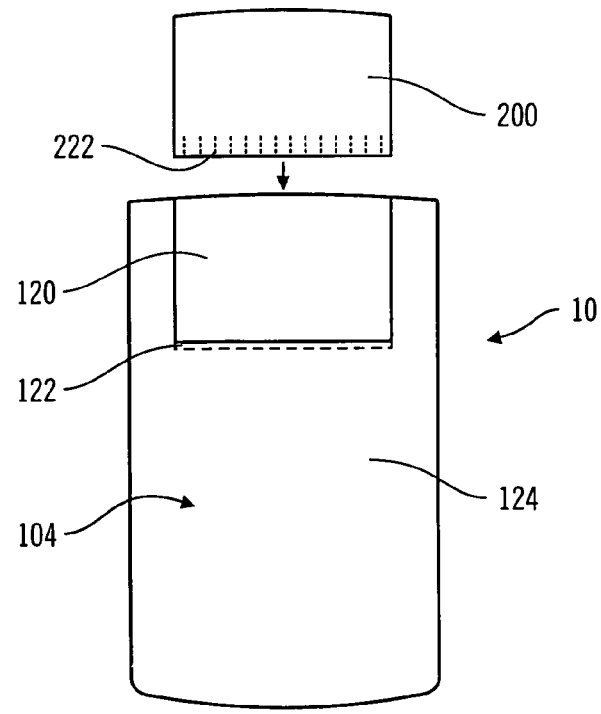
FIG. 3 is a bottom plan view of the PDA and medical device shown in FIG. 2.

FIGS. 2 and 3 are views of a PDA 10 with a medical device module 200 in accordance with an embodiment of the present invention. The PDA 10 includes a display 102 mounted in a case 104. The case includes a plurality of physical keys 106 and 108 to activate and control various features on the PDA 10. The display 102 of the PDA 10 is a touch screen LCD that allows the display of various icons 110 representative of different programs available on the PDA 10. The icons 110 on the display 102 may be activated by finger pressure or the touch of a stylus 112. The display 102 may also be used to show graphs, tabular data, animation, or the like. The display 102 also includes a region with hard icons 114 that represent regular program activating features and a writing area 116 for entering data using the stylus 112. Preferred embodiments of the PDA 10 are adapted for use of the Palm computing software and standards developed by 3 Com. However, alternative embodiments may use computing software and standards produced by other companies.

As shown in FIG. 3, the PDA 10 has a slot 120 formed in the back 124 of the case 104 of the PDA 10 for receiving the medical device module 200. The slot 120 includes connector contacts 122 that mate with corresponding contacts 222 on the medical device module 200. Thus, the PDA 10 provides a standard user interfaces, including standard PDA features and programmability, that the user knows and understands. A medical device manufacturer primarily only needs to design, build and qualify a medical device module that interfaces with a standard PDA 10 interface and uses the existing hardware of the PDA 10 to interact with the user. Therefore, a medical device manufacturer focuses primarily on a medical device module that can be interchanged by the user to provide the user with a desired capability or function on a known and/or familiar device, the PDA 10. Further embodiments (not shown) may use multiple medical device modules or a medical device module that includes more than one medical device submodule.

Figure 4:
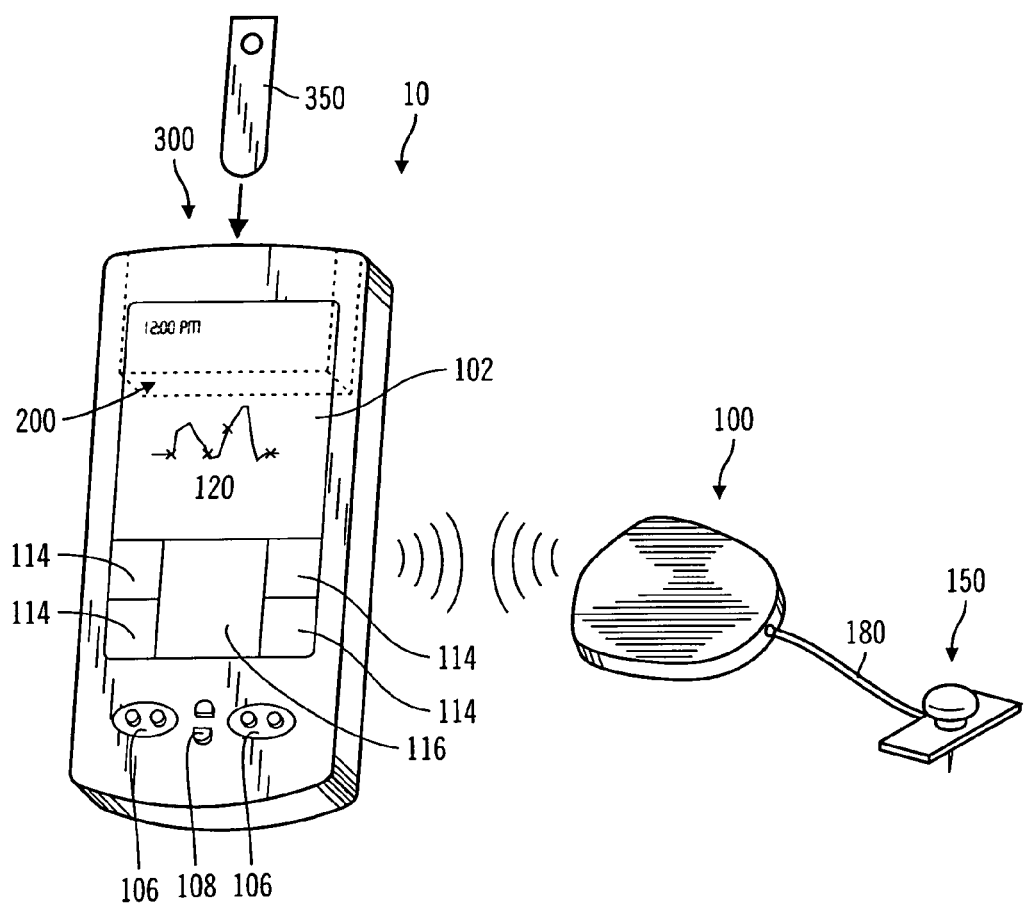
FIG. 4 is a perspective view of the PDA including a medical device module that includes a characteristic monitor and characteristic meter and that interfaces with a telemetered characteristic monitor transmitter in accordance with a first embodiment of the present invention.

FIG. 4 illustrates a perspective view of a PDA 10, in accordance with a preferred embodiment of the present invention. The PDA 10 includes a subcutaneous sensor set 150 (i.e., a sensor portion is implanted in, for example, dermal subdermal, subcutaneous tissues, or the like), a telemetered characteristic monitor transmitter 100 connected to the sensor set 150 through a sensor cable/connector 180, and a medical device module 200 that includes a characteristic monitor 200' and a characteristic meter 300. The subcutaneous sensor set 150 utilizes an electrode-type sensor, as described in more detail in U.S. Pat. No. 5,391,250, entitled "Method Of Fabricating Thin Film Sensors", U.S. Pat. No. 5,482,473, entitled "Flex Circuit Connector", U.S. Pat. No. 5,390,671, entitled "Transcutaneous Sensor Insertion Set", U.S. Pat. No. 5,568,806, entitled "Transcutaneous Sensor Insertion Set", U.S. Pat. No. 5,586,553, entitled "Transcutaneous Sensor Insertion Set", U.S. Pat. No. 5,779,655, entitled "Transducer Introducer Assembly" and co-pending U.S. Pat. No. 5,954,643, entitled "Insertion Set for a Transcutaneous Sensor," all of which are herein incorporated by reference. However, in alternative embodiments, the sensor may use other types of sensors, such as chemical based, optical based, or the like. In further alternative embodiments, the sensors may be of a type that is used on the external surface of the skin or placed just below the skin layer of the user. Preferred embodiments of a surface mounted sensor would utilize interstitial fluid harvested from underneath the skin.

The telemetered characteristic monitor transmitter 100 generally includes the capability to transmit data. However, in alternative embodiments, the telemetered characteristic monitor transmitter 100 may include a receiver, or the like, to facilitate two-way communication of data reading between the sensor set 150 and the characteristic monitor 200' of the medical device module 200. The characteristic monitor 200' in the medical device module 200 utilizes the transmitted data to determine the characteristic reading. Although a telemetered approach that utilizes RF is preferred, other wireless techniques, such as optical, IR, ultrasonic, or the like may be used. In addition, wired connections may be utilized instead of a telemetered transmission of data from the sensor 150 to the medical device module 200 (see FIG. 18 below).

The characteristic meter 300 utilizes test strips 350, or the like, with a sample obtained from the body of the patient to determine a characteristic (or analyte level) in a user at a discrete point in time. The discrete measurement from the characteristic meter 300 is stored in a memory of the medical device module 200 and may be used to calibrate the characteristic monitor 200' in the medical device module 200 against the test results from the characteristic meter 300, either in real time or using a post calibration in either the characteristic monitor 200' in the medical device module 200 or during later analysis and review once the test results have been downloaded to a separate computer, communication station, or the like. Possible characteristic meters 300 that may be used are produced by Roche Diagnostics, Bayer Corporation, Abbott Medisense, Johnson & Johnson, Mercury Diagnostics, Chronimed, or the like.

Figure 5:
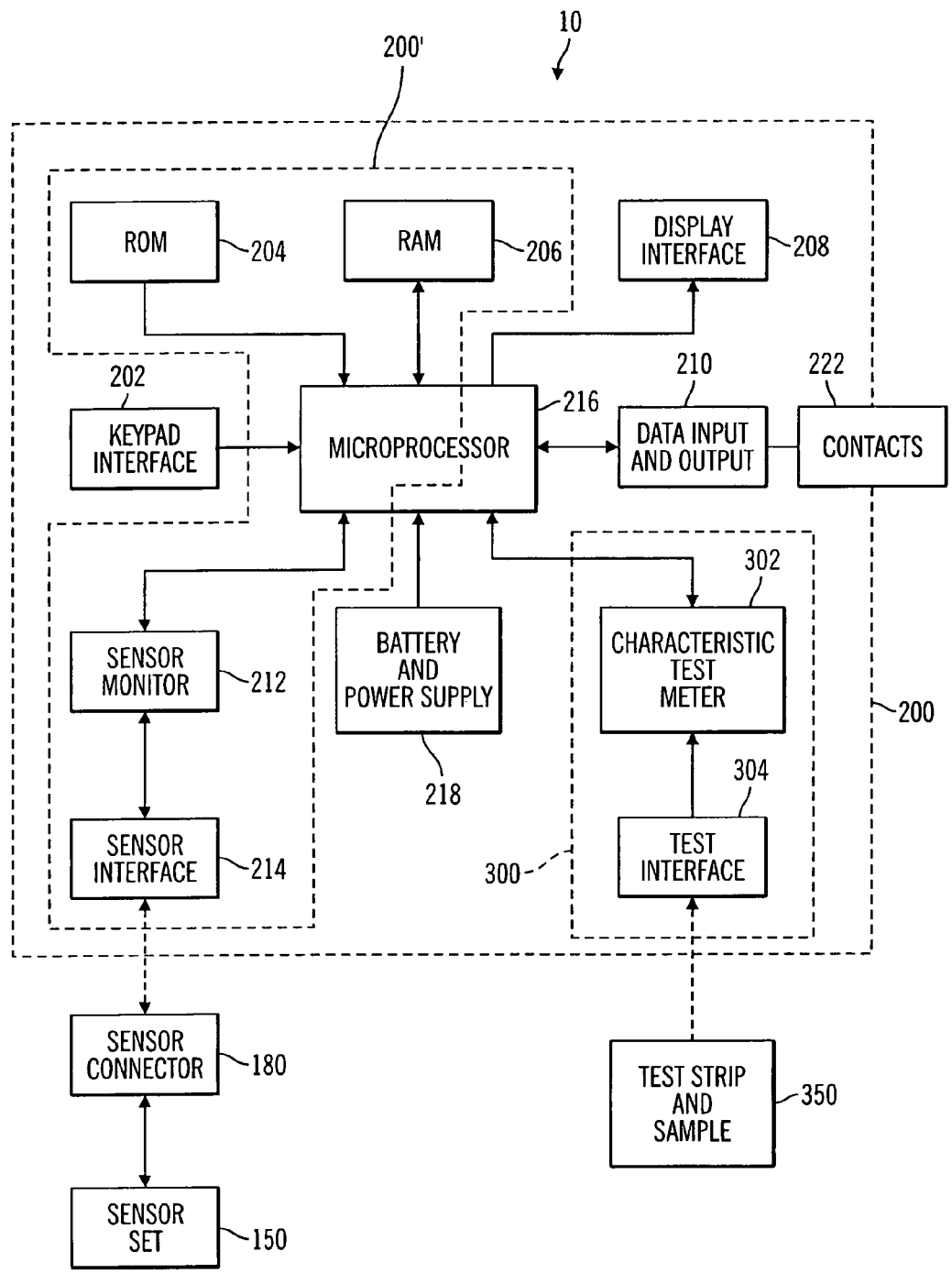
FIG. 5 is a block diagram of the medical device module that includes the characteristic monitor and the characteristic meter shown in FIG. 4.

FIG. 5 illustrates a simplified flow block diagram of the medical device module 200 shown in FIGS. 4 and 6. As shown in FIG. 5, the medical device module 200 includes the characteristic meter 300 and also the characteristic monitor 200' that interfaces with a sensor set 150. The medical device module 200 includes a keypad interface 202, a ROM 204, a RAM 206, a display interface 208, a data Input and Output (I/O) port 210 that uses the contacts 222 on the medical device module 200 to connect with the contacts 122 on the PDA 10, a sensor monitor 212, a sensor interface 214, a microprocessor 216, and a battery and/or power supply 218. An overlapping subset of these elements is used to process the data from the sensor 150 and is collectively shown as the characteristic monitor 200'. The characteristic meter 300, included in the medical device module 200, includes a characteristic test meter 302 and a test interface 304.

The microprocessor 216 of the medical device module 200 is activated in several different ways. The keypad interface 202 is coupled directly to the microprocessor 216 and is useable to activate the microprocessor 216 upon activation of the keys 106 and 108 and/or display 102 of the PDA 10. The microprocessor 216 is then prepared to store relevant information concerning the sensor data, meter readings, event data, or the like. For instance, the microprocessor 216 will store, the time, the date and the analyte level from a test strip 350 or may be used to record an independent event by the user. In addition, the keypad interface 202, unpin interfacing with the PDA 10, may be used to activate and control the microprocessor 216 to perform analysis, calibration, control the display interface 208 and display 102, download stored data and results, upload program instructions, or the like. The microprocessor 216 may also be activated by receiving a specified signal from the sensor interface 214 indicating connection or receipt of data from a sensor 150 and/or by insertion of a test strip 350 into the test interface 304 of the included characteristic meter 300. Once activated, the microprocessor 216 stores data, analyzes signal values, tests results for accuracy, calibrates, downloads data, presents data for review and analysis, provides instructions, warnings and alarms, or the like.

The microprocessor 216 is coupled to a ROM 204 and a RAM 206. In preferred embodiments, the ROM 204 is an EPROM and the RAM 206 is a static RAM; however, other comparable memory storage components such as dynamic RAM, non-static RAM, rewritable ROMs, flash memory, or the like, may be used. Generally, the ROM 204 stores the programs used by the microprocessor 216 to determine various parameters, such as the amount of an analyte corresponding to a received signal value in the sensor monitor 212 signal value, calibration techniques for adjusting the sensor signals from the sensor 150, characteristic meter 300 operation and correspondence of test results with the sensor signal values, the date and the time, and how to report information to the user. The RAM 206 is used by the microprocessor 216 to store information about the sensor signal values and test strip 350 test results for later recall by the user or the doctor. For example, a user or doctor can transcribe the stored information at a later time to determine compliance with the medical regimen or a comparison of analyte value levels to medication administration. This is accomplished by downloading the information to the display 102 through the display interface 208 and then transcribing all of the stored records at one time as they appear on the display 208. In addition, the RAM 206 may also store updated program instructions and/or patient specific information.

In preferred embodiments, the microprocessor 216 is coupled to a data input and output (I/O) port 210 that uses the contacts 222 on the medical device module 200 to connect with the contacts 122 on the PDA 10, and the user can download the stored information to an external computer (see FIG. 1), or the like, through the data I/O port 210 for evaluation, analysis, calibration, or the like. Preferably, the data I/O port 210 is capable of transferring data in both directions so that updated program instructions or reminder alarms can be set by the user or doctor. In preferred embodiments, the I/O port 210 uses the infrared (IR) technology of the PDA 10 or may include its own IR transceivers similar to those shown and described in U.S. Pat. No. 5,376,070 entitled "Data Transfer System for an Infusion Pump", or the like, which is herein incorporated by reference. However, in alternative embodiments, the I/O port 210 may use other data transfer technologies such as cables, fiber optics, RF, or the like. In still other embodiments, the data I/O port 210 may include multiple ports to support multiple communication protocols or methods, or may include a universal port capable of transmitting data in several different modes. In preferred embodiments, the stored data may be downloaded to (or new program instructions and data uploaded from) a computer, communication station, or the like. In alternative embodiments, the stored data may be downloaded to (or new program instructions and data uploaded from) an infusion pump, or the like.

The keypad interface 202 provides the user with the capability to set parameters in the medical device module using the keys 106 and 108 and/or display 102 of the PDA 10. Such capabilities include, but are not limited to, storing additional information, setting the date and the time, or setting alarms to indicate when to take the next test with the characteristic meter 300. The keypad interface 202 is used in conjunction with the display interface 208 to access the various modes, alarms, features, or the like, by utilizing methods typically employed to set the parameters on a conventional glucose meter, an infusion pump, or the like. Except this is all done through the use of a standard PDA interface.

The medical device module 200 also includes a self contained battery and power supply 218. Preferably, the medical device module 200 uses batteries (not shown) to provide power to the medical device module 200. For example, a plurality of silver oxide batteries, such as two or three, may be used. However, it is understood that different battery chemistries may be used, such as lithium, alkaline or the like, and different numbers of batteries can be used. In preferred embodiments, the batteries have a life in the range of 1 month to 1 year, and provide a low battery warning alarm. Alternative embodiments may provide longer or shorter battery lifetimes, or include a power port to permit recharging of rechargeable batteries in the medical device module 200. Further alternative embodiments may use the power supply (not shown) that is already included in the PDA 10 or recharge its own batteries through the power supplied by the cradle 22.

The ROM 204 of the medical device module 200 also stores additional programs to operate and control the characteristic meter 300. Moreover, the RAM 206 of the medical device module 200 can stores results obtained from the characteristic meter 300. As shown in FIG. 5, a test strip 350 for holding an analyte sample is inserted into the test interface 302. This activates the characteristic test meter 304 and the microprocessor 216. The characteristic test meter 304 analyzes the characteristics and sends the analysis results to the microprocessor 216, which displays the results on the display 102 and stores the results in the RAM 206 for later review.

The programs for controlling the sensor monitor 212 of the characteristic monitor 200' are also stored in the ROM 204, and sensor data signal values received by the sensor interface 214 from the sensor set 150 are processed by the sensor monitor 212 and the microprocessor 216, and then the results are stored in the RAM 206. The sensor monitor 212 and the sensor interface 214 can be activated by a wired connection to a sensor set 150 that draws power from the characteristic monitor, by receipt of a signal from the telemetered characteristic monitor transmitter 100, or by the keys 106 and 108 and/or display 102 through the keypad interface 202. Preferred embodiments use a characteristic monitor 200' (in which the system includes a Potentiostat such as sensor monitor 212) to receive the sensor signals from a telemetered characteristic monitor transmitter 100, as shown in U.S. patent application Ser. No. 09/377,472 entitled "Telemetered Characteristic Monitor System and Method of Using the Same", which is herein incorporated by reference. In alternative embodiments, the sensor signals may be received on a more infrequent (or periodic) basis from a Holter-type monitor system, as shown in U.S. patent application Ser. No. 09/246,661 entitled "An Analyte Sensor and Holter-type type Monitor System and Method of Using the Same", which is herein incorporated by reference.

Preferred embodiments store the raw received sensor signals values from the sensor monitor 212 and the test results from the characteristic test meter 304 of the characteristic meter in the RAM 206. However, alternative embodiments may also store calibrated and adjusted results in the RAM 206 for downloading, later analysis and review. Further embodiments may only store adjusted results.

Once activated, the sensor interface 214 continuously, intermittently or near continuously receives signals from the sensor set 150 that are representative of an analyte level being monitored in a user. In preferred embodiments, the sensor monitor 212 is used in conjunction with the microprocessor 216 to store, smooth the data and determine a corresponding analyte level from the signals received from the sensor interface 214. The corresponding value may be shown on the display 208. The characteristic monitor 200' of the medical device module 200 may also perform calibration of the sensor signal values using values provided by the characteristic meter 300. The calibration may be performed on a real-time basis and/or backwards recalibrated (e.g., retrospectively). In further embodiments, the microprocessor 216 monitors the sensor signals from the sensor monitor 212 to determine when the characteristic meter 300 should be used to perform tests to be used for calibration of the sensor data signals. For instance, the microprocessor 216 could indicate that the calibration test should be delayed if the sensor data signals from the sensor monitor 212 are changing too rapidly and suggest a calibration reading when the sensor data readings are relatively stable. Also, the characteristic monitor 200' of the medical device module 200 may prompt the user to perform calibration at periodic preset intervals. Alternatively, the characteristic monitor 200' of the medical device module 200 may prompt the user to perform the calibration based upon event-triggered intervals, that are either user input, such as meals, exercise, or the like, or that are trend input, such as large excursions in glucose levels, faulty or interrupted data readings, or the like.

As shown in FIGS. 1-4, the PDA 10 includes a display 102 that is used to display the results of the measurement received from the sensor in the sensor set 150 via a cable and connector 180 attached to the telemetered characteristic monitor transmitter 100, or the like. The results and information displayed includes, but is not limited to, trending information of the characteristic (e.g., rate of change of glucose), graphs of historical data, average characteristic levels (e.g., glucose), or the like. Alternative embodiments include the ability to scroll through the data. The display 102 may also be used with the key 106 and 108 on the PDA 10 to program or update data in the medical device module 200. In addition, the calibrated data using results from the characteristic meter 300 can be displayed to provide a user with updated trend and glucose level data. This may also be used to update and show differences between the newly calibrated (or additional calibration) data and the data as it was prior to the new calibration (or additional calibration).

In other embodiments, if multiple characteristic sensors are used, the individual data for each characteristic sensor may be stored and displayed to show a comparison and an average between the two characteristic sensors.

It is noted that a typical user can have somewhat diminished visual and tactile abilities due to complications from diabetes or other conditions. Thus, the display 102 and/or keys 106 and 108 are preferably configured and adapted to the needs of a user with diminished visual and tactile abilities. In alternative embodiments, the data, analyte level value, confirmation of information, or the like can be conveyed to the user by audio signals, such as beeps, speech or the like, or vibrations. Further alternatives may include a microphone (not shown) and related circuitry to allow voice activated control of the infusion device.

Additional embodiments of the present invention may include a vibrator alarm (or optional indicator such as an L.E.D.) in either, or both, the telemetered characteristic monitor transmitter 100 and the medical device module 200 to provide a tactile (vibration) alarm to the user, such as sensor set 150 malfunction, improper connection, low battery, missed message, bad data, transmitter interference, or the like. The use of a vibration alarm provides additional reminders to an audio alarm, which could be important to someone suffering an acute reaction, or where it is desirable to have non-audio alarms to preserve and conceal the presence of the characteristic monitor system 10.

Figure 7:
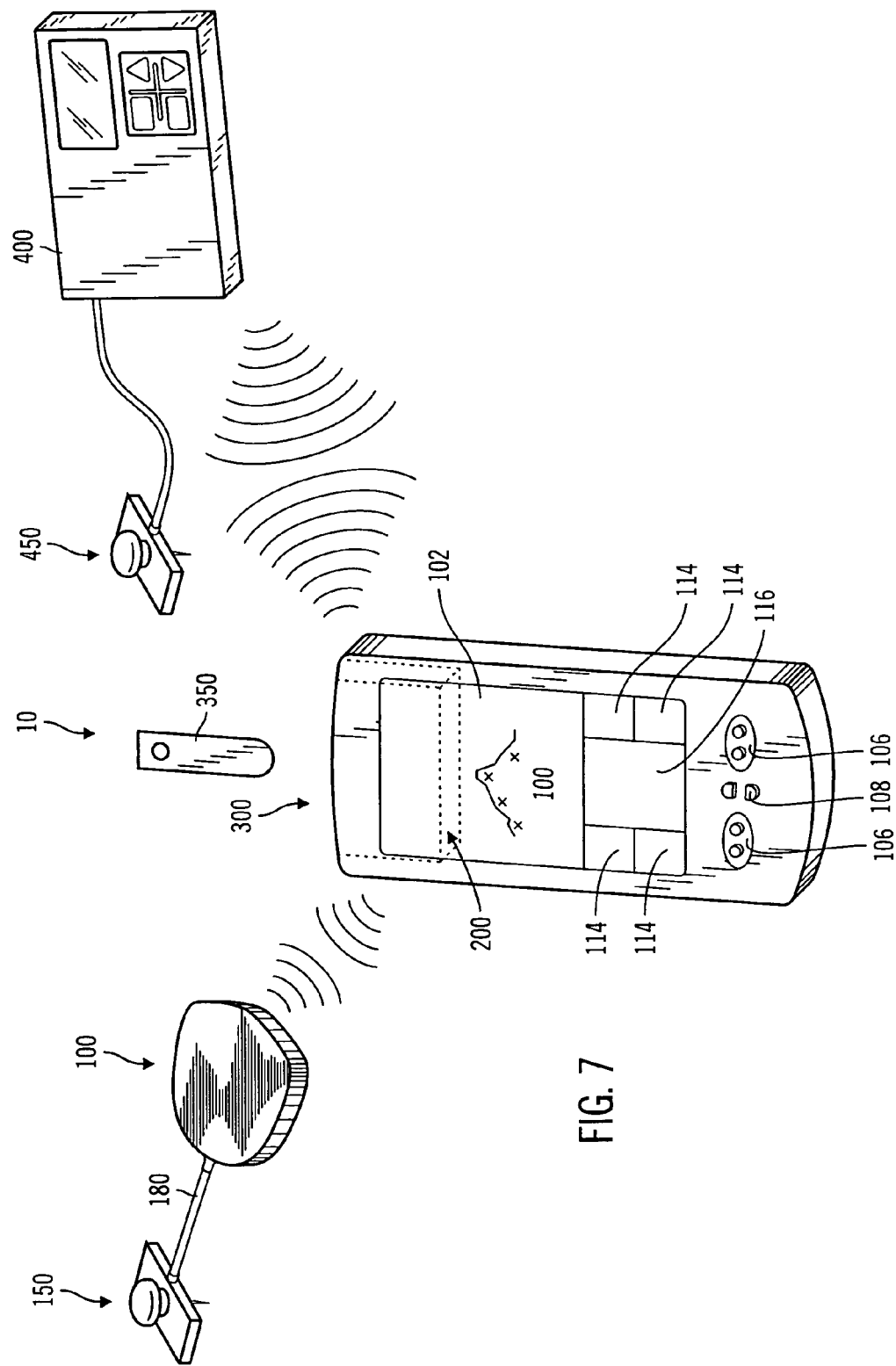
FIG. 7 is a perspective view of a PDA including a medical device module that includes a characteristic meter, characteristic monitor that interfaces with a telemetered characteristic monitor transmitter, and an infusion device in accordance with a second embodiment of the present invention.
Figure 9:
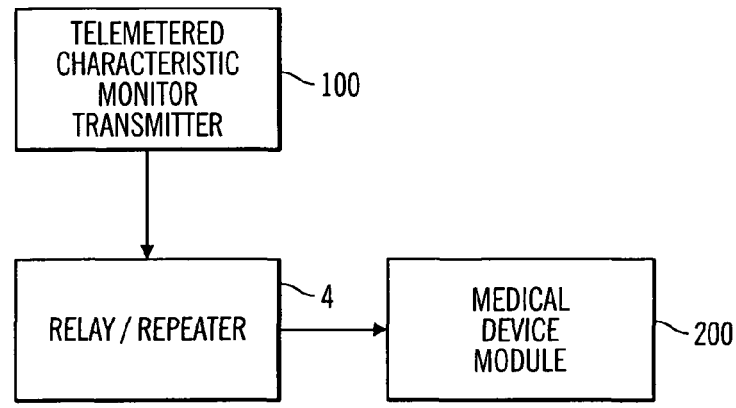
FIG. 9 is a simplified block diagram of a telemetered characteristic monitor transmitter and medical device module in accordance with a third embodiment of the present invention.
Figure 10:
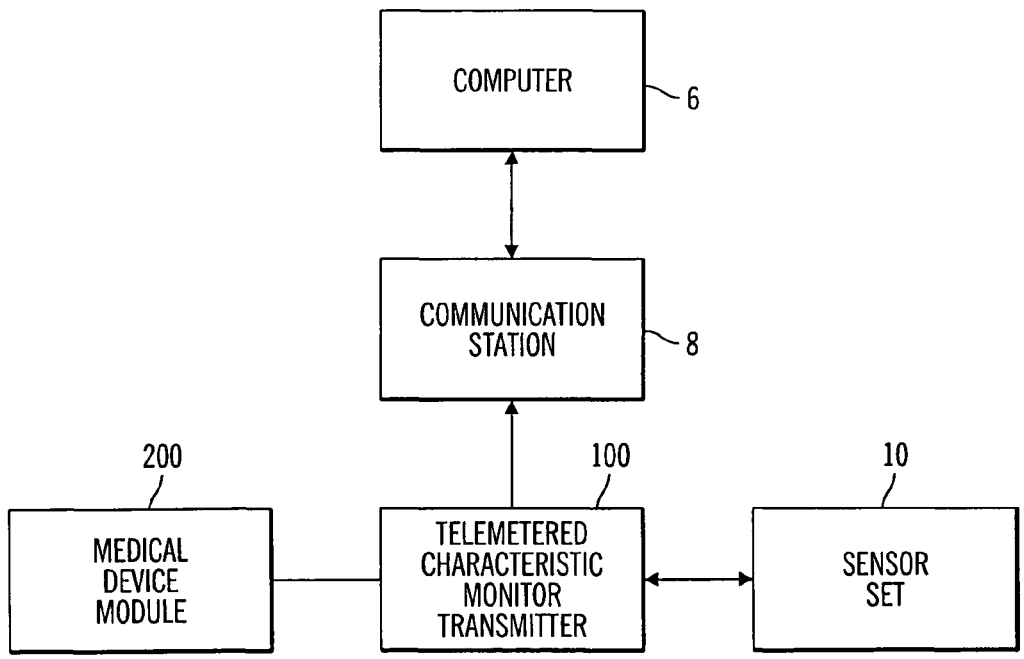
FIG. 10 is a simplified block diagram of a telemetered characteristic monitor transmitter and medical device module system in accordance with a fourth embodiment of the present invention.

FIGS. 7 and 8 show a second embodiment of the medical device module 200 may be used with a telemetered characteristic monitor transmitter 100 coupled to a sensor set 150 and an infusion pump 400 connected to an infusion set 450. In this embodiment, the medical device module 200 is also used to program and obtain data from the infusion pump 400, or the like. This further reduces the amount of equipment, the user must have, since the medical device module 200 already includes a characteristic monitor 200' and a characteristic meter 300 that will be required for calibration of the data from the telemetered characteristic monitor transmitter 100. Thus, the medical device module 200 can coordinate the sensor data and meter data with the data from the infusion pump 400, or update the delivery parameters of the infusion pump 400. The medical device module 200 may also be used to update and program the telemetered characteristic monitor transmitter 100, if the transmitter 100 includes a receiver for remote programming, calibration or data receipt. Thus, the user may need only a single device—the medical device module 200 in the PDA 10 that will receive data from a sensor set 150, perform discrete tests of an analyte with the characteristic meter 300, program and control an infusion pump 400, and operate to download data or upload programming instructions to a computer, communication station, or the like.

Figure 18:
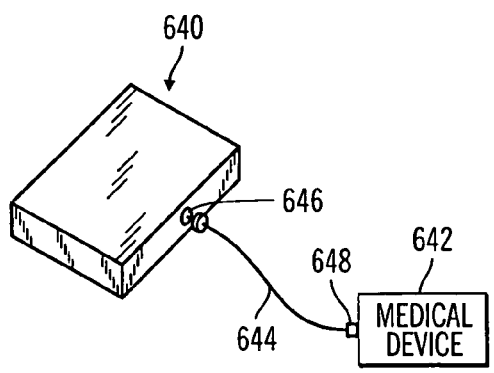
FIG. 18 is a perspective view of a medical device module that includes a input jack for a wired connection with a medical device in accordance with an eleventh embodiment of the present invention.

As discussed, the medical device module 200 can also be used to store data obtained from the sensor set 150 and then provide it to either an infusion pump 400, computer or the like for analysis. In further embodiments, the medical device module 200 can include a modem, or the like, to transfer data to and from a healthcare professional. Further embodiments, can receive updated programming or instructions via a modem connection. In addition, a relay or repeater 4 may be used with a telemetered characteristic monitor transmitter 100 and a medical device module 200 to increase the distance that the telemetered characteristic monitor transmitter 100 can be used with the medical device module 200, as shown in the third embodiment of FIG. 9. For example, the relay 4 could be used to provide information to parents of children using the telemetered characteristic monitor transmitter 100 and the sensor set 150 from a distance. The information could be used when children are in another room during sleep or doing activities in a location remote from the parents. In further embodiments, the relay 4 can include the capability to sound an alarm. In addition, the relay 4 may be capable of providing data from sensor set 150 and telemetered characteristic monitor transmitter 100 to a remotely located individual via a modem connected to the relay 4 for display on a monitor, pager or the like. In alternative embodiments, the data from the medical device module 200 and sensor set 150 may also be downloaded through a communication station 8 (or alternatively, through a medical device module 200, other data transfer device, or the like) to a remotely located computer 6 such as a PC, lap top, or the like, over communication lines, by modem or wireless connection, as shown in the fourth embodiment of FIG. 10. Also, some embodiments may omit the communication station 8 and use a direct modem or wireless connection to the computer 6. In further alternatives, either the medical device module 200 or the telemetered characteristic monitor transmitter 100 may transmit an alarm to a remotely located device, such as a communication-station, modem or the like to summon help. In addition, further embodiments of the characteristic monitor 200' of the medical device module 200 may include the capability for simultaneous monitoring of multiple sensors. Data transmission may be to other devices or include the capability to receive data or instructions from other medical devices. Preferred embodiments, as shown in FIGS. 1-8, use wireless RF frequencies; however, alternative embodiments may utilize IR, optical, ultrasonic, audible frequencies or the like. Further embodiments may also use a wired connection, as shown in FIG. 18.

Preferably, the PDA 10 uses a medical device module 200 that combines the characteristic monitor 200' and character meter 300 into a single device, but avoids an actual wired connection to the sensor set 150 by using a telemetered characteristic monitor transmitter 100. By separating the PDA 10 electronics into two separate devices; a telemetered characteristic monitor transmitter 100 (which attaches to the sensor set 150) and a characteristic monitor 200', several advantages are realized. For instance, the user can more easily conceal the presence of the PDA 10 and the telemetered characteristic monitor transmitter 100, since a wire will not be visible (or cumbersome), with clothing. In also makes it is easier to protect the medical device module 200 with a characteristic monitor 200', which can be removed from the user's body during showers, exercise, sleep or the like. In addition, the use of multiple components (e.g., transmitter 100 and medical device module 200 with a characteristic monitor 200' with a characteristic meter) facilitates upgrades or replacements, since one module or the other can be modified or replaced without requiring complete replacement of the system. Further, the use of multiple components can improve the economics of manufacturing, since some components may require replacement on a more frequent basis, sizing requirements may be different for each module, there may be different assembly environment requirements, and modifications can be made without affecting the other components. For instance, the PDA 10 with its standard interface and other uses can be mass produced at lower cost. And the medical device module 200 can be made to rigorous medical standards at lower cost than a complete device with an interface comparable to the PDA 10. This lowers the overall system costs, which permits quicker upgrades or design modifications. Thus, manufacturers can bring new devices and/or options to market in less time and cost and with less risk.

FIG. 11 is a perspective view of a medical device module 500 that interfaces with a telemetered characteristic monitor transmitter 100 in accordance with a fifth embodiment of the present invention. This medical device module 500 includes a characteristic monitor 200' as described above, and communicates with the telemetered characteristic monitor transmitter 100 to transfer data signals from a sensor set. This embodiment does not include a characteristic meter as described above. Preferably, the communication between the medical device module 500 and telemetered characteristic monitor transmitter 100 is wireless, as described above. However, in alternative embodiments, a wired connection such as shown in FIG. 18 may be used. In further alternative embodiments, the medical device module 500 may also just act as a interface and communication device for the PDA 10 to receive processed data from the telemetered characteristic monitor transmitter 100, if the telemetered characteristic monitor transmitter 100 is a fully functional characteristic monitor that includes many of the functions of the characteristic monitor 200' described above.

FIG. 12 is a perspective view of a medical device module 520 that interfaces with a characteristic meter 522 in accordance with a sixth embodiment of the present invention. Preferably, the communication between the medical device module 520 and characteristic meter 522 is wireless, as described above. However, in alternative embodiments, a wired connection such as shown in FIG. 18 may be used. This embodiment does not include a characteristic monitor 200' or a characteristic meter 300 within the medical device module, as described above. Rather, this embodiment provides an interface with the PDA 10 and communication capability between the PDA 10 and the characteristic meter 522.

FIG. 13 is a perspective view of a medical device module 540 that interfaces with an infusion device 400, telemetered characteristic monitor transmitter 100 and a characteristic meter 522 in accordance with a seventh embodiment of the present invention. This embodiment does not include a characteristic meter 300 within the medical device module, as described above. Rather, this embodiment provides an interface with the PDA 10 and communication capability between the PDA 10 and the telemetered characteristic monitor transmitter 100, the characteristic meter 522, and the infusion device 400. This medical device module 540 includes a characteristic monitor 200', and communicates with the telemetered characteristic monitor transmitter 100 to transfer data signals from a sensor set and the infusion device 400 as described above. Preferably, the communication between the medical device module 500 and telemetered characteristic monitor transmitter 100, the infusion device 400, and the characteristic meter 522 is wireless, as described above. However, in alternative embodiments, a wired connection such as shown in FIG. 18 may be used. In further alternative embodiments, the medical device module 500 may also just act as a interface and communication device for the PDA 10 to receive processed data from the telemetered characteristic monitor transmitter 100, if the telemetered characteristic monitor transmitter 100 is a fully functional characteristic monitor that includes many of the functions of the characteristic monitor 200' described above.

Figure 14:
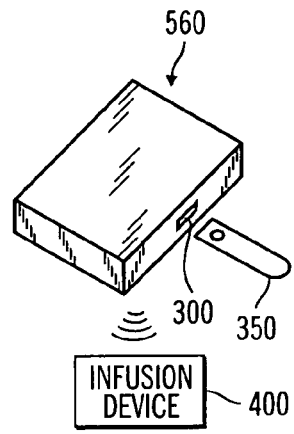
FIG. 14 is a perspective view of a medical device module that includes a characteristic meter and interfaces with an infusion device in accordance with an eighth embodiment of the present invention.

FIG. 14 is a perspective view of a medical device module 560 that includes a characteristic meter 300 and interfaces with an infusion device 400 in accordance with an eighth embodiment of the present invention. This embodiment does not include a characteristic monitor 200' within the medical device module, as described above. Rather, this embodiment provides an interface with the PDA 10 and communication capability between the PDA 10 and the infusion device 400. Preferably, the communication between the medical device module 560 and the infusion device 400 is wireless, as described above. However, in alternative embodiments, a wired connection such as shown in FIG. 18 may be used.

Figure 15:
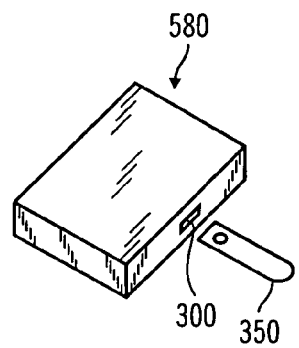
FIG. 15 is a perspective view of a medical device module that includes a characteristic meter in accordance with a ninth embodiment of the present invention.

FIG. 15 is a perspective view of a medical device module 580 that includes a characteristic meter 300 in accordance with a ninth embodiment of the present invention. This embodiment does not include the characteristic monitor 200' as described above. It is primarily adapted to providing blood glucose test capabilities to the PDA 10. Preferably, the test results and any relevant data input by the user can be downloaded, or updated program instructions can be uploaded to the medical device module 580 through either a wireless or wired connection.

Figure 16:
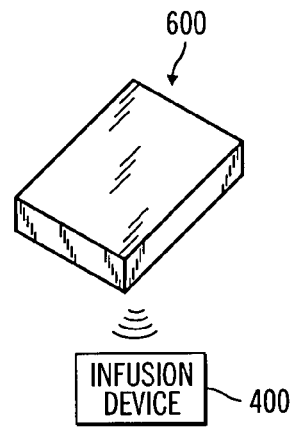
FIG. 16 is a perspective view of a medical device module that interfaces with an infusion device in accordance with a tenth embodiment of the present invention.

FIG. 16 is a perspective view of a medical device module 600 that interfaces with an infusion device in accordance with a tenth embodiment of the present invention. This embodiment does not include a characteristic monitor 200' or a characteristic meter 300 within the medical device module, as described above. Rather, this embodiment provides an interface with the PDA 10 and communication capability between the PDA 10 and the infusion device 400. Preferably, the communication between the medical device module 600 and the infusion device 400 is wireless, as described above. However, in alternative embodiments, a wired connection such as shown in FIG. 18 may be used.

Figure 17:
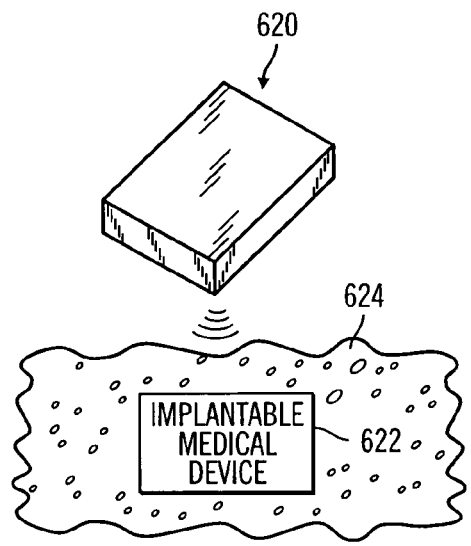
FIG. 17 is a perspective view of a medical device module that interfaces with an implantable medical device in accordance with a tenth embodiment of the present invention.

FIG. 17 is a perspective view of a medical device module 620 that interfaces with an implantable medical device 622 in accordance with a tenth embodiment of the present invention. Preferred embodiments of the implantable medical device 622 may be an infusion device, a characteristic monitor and/or sensor, a pacemaker, a neurostimulator, or the like. Generally, the devices are completely implanted in the body tissue 624 of a user. The medical device module 620 acts as an interface to the PDA 10 to communicate with and/or receive data from the implantable medical device 622. This embodiment is not shown with a characteristic monitor 200' or characteristic meter 300. However, alternative embodiments could include either or both with a characteristic monitor 200' or characteristic meter 300 as well as interfacing with the implantable medical device.

FIG. 18 is a perspective view of a medical device module 640 that includes a input jack 646 for a wired connection with a medical device 642 in accordance with an eleventh embodiment of the present invention. The medical device 642 can be any of the devices described herein. The medical device module 640 is coupled to a cable 644 through an input jack 646. The medical device 642 is also coupled to the cable 644 through an input jack 648 to complete the connection between the medical device module 640 and medical device 642. In particular embodiments, the medical device module 640 may include a modem, or the like, for facilitating the transfer of data and/or information to the medical device 642. In further embodiments, the input jack 646 is an RS-232 port. However, different types of jacks, plugs and connectors may be used. In alternative embodiments, the medical device module 640 may also include the capability to transfer data and/or information by wireless communication, as described above.

FIG. 19 is a perspective view of a medical device module 660 that interfaces with an implantable analyte sensing patch 662 in accordance with a twelfth embodiment of the present invention. As shown, the implantable patch 662 is generally implanted under the skin 664 of the user. However, in alternative embodiments, the implantable patch may be implanted in other body tissue, as described above, or attached to the skin surface of the user. Preferably, the implantable patch 662 includes a photo-reactive substance or compound 76 that optically changes, fluoresces, or the like, or other suitable compounds that detect changing properties in the presence of a bodily fluid analyte, such as glucose or the like. The compounds can also be used to detect the level of an analyte that has been ingested, injected or placed inside the body, such as marker substances, or the like. For example, possible compounds, including but not limited to, produce a fluorescent change in the presence of a bodily fluid analyte are disclosed in U.S. Pat. No. 5,503,770 issued Apr. 2, 1996 to James et al. and entitled "Fluorescent Compound Suitable For Use In The Detection Of Saccharides"; U.S. Pat. No. 5,512,246 issued Apr. 30, 1996 to Russell et al. and entitled "Method and Means for Detecting Polyhydroxyl Compounds"; U.S. Provisional Application Ser. No. 60/007,515 to Van Antwerp et al. and entitled "Minimally Invasive Chemically Amplified Optical Glucose Sensor"; and U.S. Pat. No. 6,011,984 to Van Antwerp et al. and entitled "Detection of Biological Molecules Using Chemical Amplification", all of which are herein incorporated by reference. Other compounds using Donor Acceptor fluorescent techniques may be used, such as disclosed in U.S. Pat. No. 5,628,310 issued May 13, 1997 to Rao et al. and entitled "Method and Apparatus to Perform Trans-cutaneous Analyte Monitoring"; U.S. Pat. No. 5,342,789 issued Aug. 30, 1994 to Chick et al. and entitled "Method and Device for Detecting and Quantifying Glucose in body Fluids"; and U.S. Pat. No. 5,246,867 issued Sep. 21, 1993 to Lakowicz et al. and entitled "Determination and Quantification of Saccharides by Luminescent Lifetimes and Energy Transfer", all of which are herein incorporated by reference. In still further embodiments, the medical device module may interface with the implantable patch using other communication methods, such as RF or the like.

Figure 20:
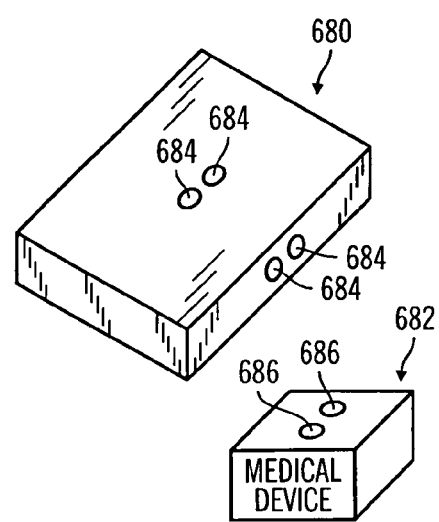
FIG. 20 is a perspective view of a medical device module that includes contacts for interfacing with a medical device in accordance with a thirteenth embodiment of the present invention.

FIG. 20 is a perspective view of a medical device module 680 that includes contacts 684 for interfacing with a medical device 682 in accordance with a thirteenth embodiment of the present invention. The medical device 682 can be any of the devices described herein. The medical device module 680 is coupled to the medical device 642 by contact 684 being coupled with corresponding contacts 686 on the medical device 642 to complete the connection between the medical device module 680 and medical device 682. In particular embodiments, the contacts 684 and 686 establish a connection by simply lining up and putting the two device together. In other embodiments, the contacts 684 and 686 are physically coupled together to reduce the likelihood that the connection will be accidentally terminated. In other embodiments, the contacts 684 are used as electrodes to measure electrical characteristics of the user. For instance, the contacts may be placed against the skin of the user to measure pulse, heart rate, sweat effects, or the like. This embodiment may utilize a wired or wireless connection to transfer data received through the contacts 684 of the medical device monitor 680 to another medical device, or the like.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A medical system, comprising:
   an external infusion device to deliver insulin to a user;
   an external characteristic meter to receive a blood sample from the user to determine a glucose level of the user;
   a sensor set to determine body characteristics on a continuous, near continuous, or intermittent basis, wherein the body characteristics include glucose levels of the user, the sensor set is coupled to a telemetered characteristic monitor transmitter to transmit sensor data including the body characteristics, and wherein the sensor set includes one of an implantable sensor, a subdermal sensor, and a subcutaneous sensor; and
   a characteristic monitor, including
      a display having a touch screen to display the sensor data received from the sensor set,
      a sensor interface to wirelessly receive the sensor data from the sensor set via the telemetered characteristic monitor transmitter, and
      a microprocessor to program and obtain data from the external infusion device, to coordinate the sensor data from the sensor set and meter data, including the determined glucose level of the user, from the external characteristic meter with the data from the external infusion device, to program and control the external infusion device, and to update delivery parameters of the external infusion device.

2. The medical system of claim 1, wherein the microprocessor further updates and programs the telemetered characteristic monitor transmitter.

3. The medical system of claim 1, wherein the microprocessor further operates to download data or upload programming instructions to a computer.

4. The medical system of claim 1, wherein the microprocessor further stores the sensor data obtained from the sensor set and provides the sensor data to the external infusion device or a computer.

5. The medical system of claim 1, where the display further displays at least one of trending information of the body characteristics, graphs of historical data, and average body characteristic levels.

6. The medical system of claim 1, wherein the microprocessor processes the sensor data received from the sensor set to determine when the characteristic meter is to be used to perform calibration of the sensor data.

7. The medical system of claim 1, wherein the characteristic meter utilizes a test strip to analyze the blood sample to determine the glucose level of the user.

8. A characteristic monitor, comprising:
   a display having a touch screen to display sensor data received from a sensor set, wherein the sensor set determines body characteristics on a continuous, near continuous, or intermittent basis, the body characteristics include glucose levels of a user, the sensor set is coupled to a telemetered characteristic monitor transmitter to transmit the sensor data including the body characteristics, and wherein the sensor set includes one of an implantable sensor, a subdermal sensor and a subcutaneous sensor;
   a sensor interface to wirelessly receive the sensor data from the sensor set via the telemetered characteristic monitor transmitter; and
   a microprocessor to program and obtain data from an external infusion device that delivers insulin to the user, to coordinate the sensor data from the sensor set and meter data from an external characteristic meter that receives a blood sample from the user to determine a glucose level of the user with the data from the external infusion device, to program and control the external infusion device, and to update delivery parameters of the external infusion device.

9. The characteristic monitor of claim 8, wherein the microprocessor further updates and programs the telemetered characteristic monitor transmitter.

10. The characteristic monitor of claim 8, wherein the microprocessor further operates to download data or upload programming instructions to a computer.

11. The characteristic monitor of claim 8, wherein the microprocessor further stores the sensor data obtained from the sensor set and provides the sensor data to the external infusion device or a computer.

12. The characteristic monitor of claim 8, where the display further displays at least one of trending information of the body characteristics, graphs of historical data, and average body characteristic levels.

13. The characteristic monitor of claim 8, wherein the microprocessor processes the sensor data received from the sensor set to determine when the characteristic meter is to be used to perform calibration of the sensor data.

14. The characteristic monitor of claim 8, wherein the characteristic meter utilizes a test strip to analyze the blood sample to determine the glucose level of the user.

* * * * *